US011098323B2

(12) United States Patent
Ellis et al.

(10) Patent No.: US 11,098,323 B2
(45) Date of Patent: Aug. 24, 2021

(54) BRASSICA EVENT MON94100 AND METHODS OF USE THEREOF

(71) Applicant: Monsanto Technology LLC, St. Louis, MO (US)

(72) Inventors: Christine M. Ellis, Manchester, MO (US); Shirley X. Guo, Chesterfield, MO (US); Sherry LeClere, Ballwin, MO (US); Mingsheng Peng, Wildwood, MO (US); Janice R. Weihe, New Baden, IL (US)

(73) Assignee: Monsanto Technology LLC, St. Louis, MO (US)

( * ) Notice: Subject to any disclaimer, the term of this patent is extended or adjusted under 35 U.S.C. 154(b) by 0 days.

(21) Appl. No.: 16/601,409

(22) Filed: Oct. 14, 2019

(65) Prior Publication Data

US 2020/0123559 A1    Apr. 23, 2020

Related U.S. Application Data

(60) Provisional application No. 62/746,158, filed on Oct. 16, 2018.

(51) Int. Cl.
| | |
|---|---|
| *C12N 15/82* | (2006.01) |
| *A01H 6/20* | (2018.01) |
| *A01N 37/10* | (2006.01) |
| *A01H 5/10* | (2018.01) |

(52) U.S. Cl.
CPC .......... *C12N 15/8274* (2013.01); *A01H 5/10* (2013.01); *A01H 6/20* (2018.05); *A01N 37/10* (2013.01); *C12N 15/8271* (2013.01)

(58) Field of Classification Search
CPC .................. C12N 15/8271; C12N 15/8274
See application file for complete search history.

(56) References Cited

U.S. PATENT DOCUMENTS

| | | | | |
|---|---|---|---|---|
| 6,613,963 | B1 * | 9/2003 | Gingera | A01H 5/00 435/418 |
| 8,501,407 | B2 * | 8/2013 | Brinker | C12Q 1/6895 435/6.11 |

FOREIGN PATENT DOCUMENTS

| | | |
|---|---|---|
| WO | 2011034704 A1 | 3/2011 |
| WO | WO2012071039 A1 | 5/2012 |
| WO | 2016173540 A1 | 11/2016 |

OTHER PUBLICATIONS

Invitation to Pay Additional Fees regarding PCT Application No. PCT/US2019/56141, mailed Dec. 26, 2019, 2 pages.
International Search Report and Written Opinion regarding PCT Application No. PCT/US2019/56141, dated Feb. 20, 2020.

* cited by examiner

*Primary Examiner* — Mykola V. Kovalenko
(74) *Attorney, Agent, or Firm* — Dentons US LLP; Lawrence Lavin

(57) ABSTRACT

The invention provides recombinant DNA molecules that are unique to *Brassica* Event MON94100 and transgenic *Brassica* plants, *Brassica* plant parts, *Brassica* seeds, *Brassica* cells, and agricultural products containing *Brassica* Event MON94100 as well as methods of using and detecting *Brassica* Event MON94100. Transgenic *Brassica* plants containing *Brassica* Event MON94100 exhibit tolerance to dicamba.

3 Claims, 2 Drawing Sheets

Specification includes a Sequence Listing.

SEQ ID NO: 9

| RB | P-PCSV | L-TEV | TS-Ps.RbcS | CS-STEma.DMO | T-Mt.AC | LB |

Figure 2

SEQUENCE LISTING

```
<160> NUMBER OF SEQ ID NOS: 13

<210> SEQ ID NO 1
<211> LENGTH: 30
<212> TYPE: DNA
<213> ORGANISM: Artificial Sequence
<220> FEATURE:
<223> OTHER INFORMATION: Chimeric DNA molecule of Brassica genomic DNA
      and transgene DNA

<400> SEQUENCE: 1
tcacttgttt tgacaccagt cagcatcatc                                      30

<210> SEQ ID NO 2
<211> LENGTH: 30
<212> TYPE: DNA
<213> ORGANISM: Artificial Sequence
<220> FEATURE:
<223> OTHER INFORMATION: Chimeric DNA molecule of Brassica genomic DNA
      and transgene DNA

<400> SEQUENCE: 2
acaattgaat atatcctagc aagcattatt                                      30

<210> SEQ ID NO 3
<211> LENGTH: 60
<212> TYPE: DNA
<213> ORGANISM: Artificial Sequence
<220> FEATURE:
<223> OTHER INFORMATION: Chimeric DNA molecule of Brassica genomic DNA
      and transgene DNA

<400> SEQUENCE: 3
ccaaaataac gacagtcact tgttttgaca ccagtcagca tcatcacacc aaaagttagg      60

<210> SEQ ID NO 4
<211> LENGTH: 60
<212> TYPE: DNA
<213> ORGANISM: Artificial Sequence
<220> FEATURE:
<223> OTHER INFORMATION: Chimeric DNA molecule of Brassica genomic DNA
      and transgene DNA

<400> SEQUENCE: 4
gacatgaagc catttacaat tgaatatatc ctagcaagca ttattaacct atctctcaac      60

<210> SEQ ID NO 5
```

<211> LENGTH: 100
<212> TYPE: DNA
<213> ORGANISM: Artificial Sequence
<220> FEATURE:
<223> OTHER INFORMATION: Chimeric DNA molecule of Brassica genomic DNA and transgene DNA

<400> SEQUENCE: 5

```
caccatctaa tgaatagtca ccaaaataac gacagtcact tgttttgaca ccagtcagca    60
tcatcacacc aaaagttagg cccgaatagt ttgaaattag                         100
```

<210> SEQ ID NO 6
<211> LENGTH: 100
<212> TYPE: DNA
<213> ORGANISM: Artificial Sequence
<220> FEATURE:
<223> OTHER INFORMATION: Chimeric DNA molecule of Brassica genomic DNA and transgene DNA

<400> SEQUENCE: 6

```
tgatccatgt agatttcccg gacatgaagc catttacaat tgaatatatc ctagcaagca    60
ttattaacct atctctcaac gctgtcgttt agagatgtac                         100
```

<210> SEQ ID NO 7
<211> LENGTH: 1104
<212> TYPE: DNA
<213> ORGANISM: Artificial Sequence
<220> FEATURE:
<223> OTHER INFORMATION: Chimeric DNA molecule of Brassica genomic DNA and transgene DNA

<400> SEQUENCE: 7

```
acgagcccta cgcaaagtta tttatattca gtcattcccc ttaggtatta tcttccaaac    60
aatctaagtt ttatgaaaaa tcgcatacta tacgaagaat acctcttagg gatgcaaaat   120
gttcctcctc cgttacactt ccatccaaat atttaacgtc accgatattg aaaggacttc   180
tacagaggaa ctggtatta gccacattcc gagccccgta tgtgatacaa agttggacta    240
cgtttgtcca ttcttgcaca ctcatcacga ccaccacgtc atcagaagtt actatgtttg    300
atggttgaga agttgattga atcccatgca acattccgtc aggcagttga tatgtcaaag   360
caacggggca ttcaggtcca ataaccagct cttcgcgtat gagagacgta aaggagtcga   420
tatttttgtt ggtgcgtgca actatatact gctccactat gccaggatct ccctcgaatt   480
gccaacaacc ggccgcactt ttattccact ttccaattct aattcgtaca agctgaccca   540
tctgcagaca aagtaaacga tgatgaccat aatatagaa attatgaaac ttaattaatg    600
ttcctctgtt ctccgaataa attttcctac tatcatgtca tacccagata catgggtagc   660
attaaatgac taaagtggag cactcaccta tattttgtag cctccttccc cagccctcac   720
aattgattac tatattaaag cgatacctgc agatttcttg aaaatatgtt gtgtctaatc   780
tatggaacac ctttactcct tatttatagt gcatttaga ctgaggactc tacataaaac    840
gtatgtatct cattaaggaa gcgtgtcttc tcccctcct ttaattaccc aagactttcg    900
cttggattga agcacagat ttgataagtc tccaatgaat agttacatat caccatctaa    960
tgaatagtca ccaaaataac gacagtcact tgttttgaca ccagtcagca tcatcacacc  1020
aaaagttagg cccgaatagt ttgaaattag aaagctcgca attgaggtct gtcgaccctg  1080
caggtacact ggcgcgccgg ccgc                                         1104
```

<210> SEQ ID NO 8

<211> LENGTH: 1281
<212> TYPE: DNA
<213> ORGANISM: Artificial Sequence
<220> FEATURE:
<223> OTHER INFORMATION: Chimeric DNA molecule of Brassica genomic DNA and transgene DNA

<400> SEQUENCE: 8

| | | | | | |
|---|---|---|---|---|---|
| ctcatctaag | cccccatttg | gacgtgaatg | tagacacgtc | gaaataaaga | tttccgaatt | 60 |
| agaataattt | gtttattgct | ttcgcctata | aatacgacgg | atcgtaattt | gtcgttttat | 120 |
| caaaatgtac | tttcatttta | taataacgct | gcggacatct | acattttga | attgaaaaaa | 180 |
| aattggtaat | tactctttct | tttctccat | attgaccatc | atactcattg | ctgatccatg | 240 |
| tagatttccc | ggacatgaag | ccatttacaa | ttgaatatat | cctagcaagc | attattaacc | 300 |
| tatctctcaa | cgctgtcgtt | tagagatgta | cttatcgaat | ctgaaatcta | tttatcatcc | 360 |
| atcattcaat | tcagtcttcg | ctattattta | cacctccatc | taaatttata | tcgaatatct | 420 |
| cgtcaacaaa | aataaagtaa | cgtcacaaga | tttaactcga | tacgttagtc | tcgttttata | 480 |
| aataaaccag | aaattaatct | cttaatgcta | atcacgacgt | ctgagactca | ttttttagtag | 540 |
| caccaatgtt | tgaattccat | gctgcacgtt | ccttcctaga | cacttaaatg | ggatagcggg | 600 |
| aatactcact | actacctttc | acatttcacc | atttgcatat | gtacggcgta | gctgccaaga | 660 |
| gatatggcgg | aacatgcata | tgggtgataa | tgagtaaccc | tttatcccat | ttcagtgact | 720 |
| tttacaagtt | tccttgtaaa | aaggaatatg | accacggcgc | atctttcaga | tttacttaaa | 780 |
| cttcactcga | tatgttgtat | gtaatagtgt | atgatgacaa | tgggtttctc | ctctatatat | 840 |
| agccggtcgt | gcttgcaccc | acacccctag | attatactga | aaacaaatcc | tattttatat | 900 |
| gtggtgttat | ataccaccac | gtctccacct | tcatggaaca | cgtattgtct | cgtcaaactt | 960 |
| taaactgaat | tttgcaagtt | caagtgtaac | cggttgcagg | tttttggga | attagataag | 1020 |
| acttatggtt | aagaggtcaa | atcagtcatt | ccaccttggt | agaactacaa | gttctccaat | 1080 |
| tattaaaaaa | taagcttagt | cctgtaattt | cgaaatttgc | tatgtatatt | cagtataatg | 1140 |
| agccttattc | aaataataat | tcgagcgaat | aataataaaa | atggatttaa | aaataatatt | 1200 |
| gataaactga | gaaaaatgac | aatgcatggc | tttttctgta | gatgtctttt | tccgcacaag | 1260 |
| ttattcaaat | aataattcga | t | | | | 1281 |

<210> SEQ ID NO 9
<211> LENGTH: 2913
<212> TYPE: DNA
<213> ORGANISM: Artificial Sequence
<220> FEATURE:
<223> OTHER INFORMATION: Transgene insert

<400> SEQUENCE: 9

| | | | | | |
|---|---|---|---|---|---|
| ccagtcagca | tcatcacacc | aaaagttagg | cccgaatagt | ttgaaattag | aaagctcgca | 60 |
| attgaggtct | gtcgaccctg | caggtacact | ggcgcgccgg | ccgcagatct | tgagccaatc | 120 |
| aaagaggagt | gatgtagacc | taaagcaata | atggagccat | gacgtaaggg | cttacgccca | 180 |
| tacgaaataa | ttaaaggctg | atgtgacctg | tcggtctctc | agaaccttta | cttttttatgt | 240 |
| ttggcgtgta | ttttaaatt | tccacggcaa | tgacgatgtg | acccaacgag | atcttgagcc | 300 |
| aatcaaagag | gagtgatgta | gacctaaagc | aataatggag | ccatgacgta | agggcttacg | 360 |
| cccatacgaa | ataattaaag | gctgatgtga | cctgtcggtc | tctcagaacc | tttactttt | 420 |
| atatttggcg | tgtattttta | aatttccacg | gcaatgacga | tgtgacctgt | gcatccgctt | 480 |

| | |
|---|---|
| tgcctataaa taagttttag tttgtattga tcgacacggt cgagaagaca cggccataag | 540 |
| cttggatcct cgagaattct caacacaaca tatacaaaac aaacgaatct caagcaatca | 600 |
| agcattctac ttctattgca gcaatttaaa tcatttcttt taaagcaaaa gcaattttct | 660 |
| gaaaattttc accatttacg aacgatagcc atggcttcta tgatatcctc ttccgctgtg | 720 |
| acaacagtca gccgtgcctc taggggggcaa tccgccgcaa tggctccatt cggcggcctc | 780 |
| aaatccatga ctggattccc agtgaggaag gtcaacactg acattacttc cattacaagc | 840 |
| aatggtggaa gagtaaagtg catgcaggtg tggcctccaa ttggaaagaa gaagtttgag | 900 |
| actctttcct atttgccacc attgacgaga gattcccggg ccatggccac cttcgtccgc | 960 |
| aatgcctggt atgtggcggc gctgcccgag gaactgtccg aaaagccgct cggccggacg | 1020 |
| attctcgaca caccgctcgc gctctaccgc cagcccgacg tgtggtcgc ggcgctgctc | 1080 |
| gacatctgtc cgcaccgctt cgcgccgctg agcgacggca tcctcgtcaa cggccatctc | 1140 |
| caatgcccct atcacgggct ggaattcgat ggcggcgggc agtgcgtcca taacccgcac | 1200 |
| ggcaatggcg cccgcccggc ttcgctcaac gtccgctcct tcccggtggt ggagcgcgac | 1260 |
| gcgctgatct ggatctgtcc cggcgatccg gcgctggccg atcctggggc gatccccgac | 1320 |
| ttcggctgcc gcgtcgatcc cgcctatcgg accgtcggcg gctatgggca tgtcgactgc | 1380 |
| aactacaagc tgctggtcga caacctgatg gacctcggcc acgcccaata tgtccatcgc | 1440 |
| gccaacgccc agaccgacgc cttcgaccgg ctggagcgcg aggtgatcgt cggcgacggt | 1500 |
| gagatacagg cgctgatgaa gattcccggc ggcacgccga gcgtgctgat ggccaagttc | 1560 |
| ctgcgcggcg ccaataccc cgtcgacgct tggaacgaca tccgctggaa caaggtgagc | 1620 |
| gcgatgctca acttcatcgc ggtggcgccg gaaggcaccc cgaaggagca gagcatccac | 1680 |
| tcgcgcggta cccatatcct gacccccgag acggaggcga gctgccatta tttcttcggc | 1740 |
| tcctcgcgca atttcggcat cgacgatccg gagatggacg gcgtgctgcg cagctggcag | 1800 |
| gctcaggcgc tggtcaagga ggacaaggtc gtcgtcgagg cgatcgagcg ccgccgcgcc | 1860 |
| tatgtcgagg cgaatggcat ccgcccggcg atgctgtcgt gcgacgaagc cgcagtccgt | 1920 |
| gtcagccgcg agatcgagaa gcttgagcag ctcgaagccg cctgaaccgg cttatgctgc | 1980 |
| acgggcgggg cggggcggtt tcgatcggct cgcctgtccc ggcgatattc tagcttaatc | 2040 |
| atctgaaact gttcaccatg catgcaatct tgtgaaatat atggttttaa ttagacttca | 2100 |
| atcttatgtt ggctattgta ctaataaaag catgtcatgt tattttcatt tgattttatc | 2160 |
| tgtactttgg tttgtttgaa gaataaagat gagcttgcta tgcatgcatg catgccatcg | 2220 |
| attatcaggg tttcctttttt tcttttctgg cttcccatca atttggtgtg aattagtgtg | 2280 |
| tgtgatatat tatattatgc tatttatgaa ataaattgtt ggttatattt gatctacaat | 2340 |
| ctacatacat gtgattttta tcaacaaaat atctcgggaa acaataccttt tttggtagca | 2400 |
| aaattcaaat aatactattt taaataaatc aaagttaacc aataccttat tcaagttgga | 2460 |
| ggggtctcaa acaagcaaaa gaattcaagt tgttaatgaa cttcggttaa tgataaaaga | 2520 |
| attcgcattt aaaagcggcc gcacgtcctg cttggcctac taggccaacg caggcgctgg | 2580 |
| ccgtgacggc cacgagcgaa ctaggccttg gccgcatcg atcgtgaagt ttctcatcta | 2640 |
| agcccccatt tggacgtgaa tgtagacacg tcgaaataaa gatttccgaa ttagaataat | 2700 |
| ttgtttattg ctttcgccta taaatacgac ggatcgtaat ttgtcgtttt atcaaaatgt | 2760 |
| actttcattt tataataacg ctgcggacat ctacattttt gaattgaaaa aaaattggta | 2820 |
| attactcttt cttttttctcc atattgacca tcatactcat tgctgatcca tgtagatttc | 2880 |

```
                                                    ccggacatga agccatttac aattgaatat atc                     2913
```

<210> SEQ ID NO 10
<211> LENGTH: 4913
<212> TYPE: DNA
<213> ORGANISM: Artificial Sequence
<220> FEATURE:
<223> OTHER INFORMATION: Chimeric DNA molecule of Brassica genomic DNA
      and transgene DNA

<400> SEQUENCE: 10

```
acgagcccta cgcaaagtta tttatattca gtcattcccc ttaggtatta tcttccaaac    60
aatctaagtt ttatgaaaaa tcgcatacta tacgaagaat acctcttagg gatgcaaaat   120
gttcctcctc cgttacactt ccatccaaat atttaacgtc accgatattg aaaggacttc   180
tacagaggaa ctggtattta gccacattcc gagcccgta tgtgatacaa agttggacta    240
cgtttgtcca ttcttgcaca ctcatcacga ccaccacgtc atcagaagtt actatgtttg   300
atggttgaga agttgattga atcccatgca acattccgtc aggcagttga tatgtcaaag   360
caacggggca ttcaggtcca ataaccagct cttcgcgtat gagagacgta aaggagtcga   420
tattttttgtt ggtgcgtgca actatatact gctccactat gccaggatct ccctcgaatt   480
gccaacaacc ggccgcactt ttattccact ttccaattct aattcgtaca agctgaccca   540
tctgcagaca agtaaacga tgatgaccat taatatagaa attatgaaac ttaattaatg    600
ttcctctgtt ctccgaataa attttcctac tatcatgtca tacccagata catgggtagc   660
attaaatgac taaagtggag cactcaccta tattttgtag cctccttccc cagccctcac    720
aattgattac tatattaaag cgatacctgc agatttcttg aaaatatgtt gtgtctaatc   780
tatgaacac ctttactcct tatttatagt gcattttaga ctgaggactc tacataaaac    840
gtatgtatct cattaaggaa gcgtgtcttc tcccctcct ttaattaccc aagactttcg    900
cttggattga agcacagat ttgataagtc tccaatgaat agttacatat caccatctaa    960
tgaatagtca ccaaaataac gacagtcact tgttttgaca ccagtcagca tcatcacacc   1020
aaaagttagg cccgaatagt ttgaaattag aaagctcgca attgaggtct gtcgaccctg   1080
caggtacact ggcgcgccgg ccgcagatct tgagccaatc aaagaggagt gatgtagacc   1140
taaagcaata atggagccat gacgtaaggg cttacgccca tacgaaataa ttaaaggctg   1200
atgtgacctg tcggtctctc agaaccttta cttttatgt ttggcgtgta tttttaaatt    1260
tccacggcaa tgacgatgtg acccaacgag atcttgagcc aatcaaagag gagtgatgta   1320
gacctaaagc aataatggag ccatgacgta agggcttacg cccatacgaa ataattaaag   1380
gctgatgtga cctgtcggtc tctcagaacc tttactttt atatttggcg tgtattttta   1440
aatttccacg gcaatgacga tgtgacctgt gcatccgctt tgcctataaa taagttttag   1500
tttgtattga tcgacacggt cgagaagaca cggccataag cttggatcct cgagaattct   1560
caacacaaca tatacaaaac aaacgaatct caagcaatca agcattctac ttctattgca   1620
gcaatttaaa tcatttcttt taaagcaaaa gcaattttct gaaaattttc accatttacg   1680
aacgatagcc atggcttcta tgatatcctc ttccgctgtg acaacagtca gccgtgcctc   1740
tagggggcaa tccgccgcaa tggctccatt cggcggcctc aaatccatga ctggattccc   1800
agtgaggaag gtcaacactg acattacttc cattacaagc aatggtggaa gagtaaagtg   1860
catgcaggtg tggcctccaa ttggaaagaa gaagtttgag actcttttcct atttgccacc   1920
attgacgaga gattcccggg ccatggccac cttcgtccgc aatgcctggt atgtggcggc   1980
```

```
gctgcccgag gaactgtccg aaaagccgct cggccggacg attctcgaca caccgctcgc   2040
gctctaccgc cagcccgacg gtgtggtcgc ggcgctgctc gacatctgtc cgcaccgctt   2100
cgcgccgctg agcgacggca tcctcgtcaa cggccatctc caatgcccct atcacgggct   2160
ggaattcgat ggcggcgggc agtgcgtcca taacccgcac ggcaatggcg cccgcccggc   2220
ttcgctcaac gtccgctcct tcccggtggt ggagcgcgac cgctgatct ggatctgtcc    2280 cggcgatccg cgctggccg atcctggggc gatccccgac ttcggctgcc cgtcgatcc    2340 cgcctatcgg accgtcggcg gctatgggca tgtcgactgc aactacaagc tgctggtcga   2400
caacctgatg gacctcggcc acgcccaata tgtccatcgc gccaacgccc agaccgacgc   2460
cttcgaccgg ctggagcgcg aggtgatcgt cggcgacggt gagatacagg cgctgatgaa   2520
gattcccggc ggcacgccga gcgtgctgat ggccaagttc ctgcgcggcg ccaatacccc   2580
cgtcgacgct tggaacgaca tccgctggaa caaggtgagc gcgatgctca acttcatcgc   2640
ggtggcgccg gaaggcaccc cgaaggagca gagcatccac tcgcgcggta cccatatcct   2700 gaccccgag acggaggcga gctgccatta tttcttcggc tcctcgcgca atttcggcat    2760
cgacgatccg gagatggacg gcgtgctgcg cagctggcag gctcaggcgc tggtcaagga   2820
ggacaaggtc gtcgtcgagg cgatcgagcg ccgccgcgcc tatgtcgagg cgaatggcat   2880
ccgcccggca tgctgtcgt gcgacgaagc cgcagtccgt gtcagccgcg agatcgagaa    2940
gcttgagcag ctcgaagccg cctgaaccgg cttatgctgc acgggcgggg cggggcggtt   3000
tcgatcggct cgcctgtccc ggcgatattc tagcttaatc atctgaaact gttcaccatg   3060
catgcaatct tgtgaaatat atggttttaa ttagacttca atcttatgtt ggctattgta   3120
ctaataaaag catgtcatgt tattttcatt tgattttatc tgtactttgg tttgtttgaa   3180
gaataaagat gagcttgcta tgcatgcatg catgccatcg attatcaggg tttccttttt   3240
tcttttctgg cttcccatca atttggtgtg aattagtgtg tgtgatatat tatattatgc   3300
tatttatgaa ataaattgtt ggttatattt gatctacaat ctacatacat gtgatttta    3360 tcaacaaaat atctcgggaa acaataccct tttggtagca aaattcaaat aatactattt   3420
taaataaatc aaagttaacc aataccttat tcaagttgga ggggtctcaa acaagcaaaa   3480
gaattcaagt tgttaatgaa cttcggttaa tgataaaaga attcgcattt aaaagcggcc   3540
gcacgtcctg cttggcctac taggccaacg caggcgctgg ccgtgacggc cacgagcgaa   3600
ctaggccttg ggccgcatcg atcgtgaagt ttctcatcta agcccccatt tggacgtgaa   3660
tgtagacacg tcgaaataaa gatttccgaa ttagaataat ttgtttattg ctttcgccta   3720
taaatacgac ggatcgtaat ttgtcgtttt atcaaaatgt actttcattt tataataacg   3780
ctgcggacat ctacattttt gaattgaaaa aaaattggta attactcttt ctttttctcc   3840
atattgacca tcatactcat tgctgatcca tgtagatttc ccggacatga agccatttac   3900
aattgaatat atcctagcaa gcattattaa cctatctctc aacgctgtcg tttagagatg   3960
tacttatcga atctgaaatc tatttatcat ccatcattca attcagtctt cgctattatt   4020
tacacctcca tctaaattta tatcgaatat ctcgtcaaca aaaataaagt aacgtcacaa   4080
gatttaactc gatacgttag tctcgtttta taaataaacc agaaattaat ctcttaatgc   4140
taatcacgac gtctgagact cattttagt agcaccaatg tttgaattcc atgctgcacg    4200
ttccttccta gacacttaaa tgggatagcg ggaatactca ctactacctt tcacatttca   4260
ccatttgcat atgtacggcg tagctgccaa gagatatggc ggaacatgca tatgggtgat   4320
```

-continued

```
aatgagtaac cctttatccc atttcagtga cttttacaag tttccttgta aaaggaata      4380 tgaccacggc gcatctttca gatttactta aacttcactc gatatgttgt atgtaatagt      4440
gtatgatgac aatgggtttc tcctctatat atagccggtc gtgcttgcac ccacacccct      4500
agattatact gaaaacaaat cctattttat atgtggtgtt ataccacc acgtctccac       4560 cttcatggaa cacgtattgt ctcgtcaaac tttaaactga attttgcaag ttcaagtgta      4620
accggttgca ggttttttgg gaattagata agacttatgg ttaagaggtc aaatcagtca     4680
ttccaccttg gtagaactac aagttctcca attattaaaa aataagctta gtcctgtaat    4740
ttcgaaattt gctatgtata ttcagtataa tgagccttat tcaaataata attcgagcga     4800
ataataataa aaatggattt aaaaataata ttgataaact gagaaaaatg acaatgcatg    4860 gcttttctg tagatgtctt tttccgcaca agttattcaa ataataattc gat            4913
```

```
<210> SEQ ID NO 11
<211> LENGTH: 23
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 11
aaacgacagc gttgagagat agg                                              23

<210> SEQ ID NO 12
<211> LENGTH: 26
<212> TYPE: DNA
<213> ORGANISM: Artificial Sequence
<220> FEATURE:
<223> OTHER INFORMATION: Chemically Synthesized Oligonucleotide PCR
      Primer

<400> SEQUENCE: 12
ccatattgac catcatactc attgct                                           26

<210> SEQ ID NO 13
<211> LENGTH: 16
<212> TYPE: DNA
<213> ORGANISM: Artificial Sequence
<220> FEATURE:
<223> OTHER INFORMATION: Chemically Synthesized Oligonucleotide PCR
      Probe

<400> SEQUENCE: 13
atccatgtag atttcc                                                      16
```

BRASSICA EVENT MON94100 AND METHODS OF USE THEREOF

CROSS-REFERENCE TO RELATED APPLICATIONS

This application claims the benefit of priority of U.S. Provisional Application No. 62/746,158, filed Oct. 16, 2018, the disclosure of which is hereby incorporated by reference in its entirety.

INCORPORATION OF SEQUENCE LISTING

The sequence listing that is contained in the file named "MONS450US_ST25", which is 16,483 bytes (measured in MS-Windows) and created on Sep. 12, 2019, is filed herewith by electronic submission and incorporated herein by reference.

FIELD OF THE INVENTION

The invention relates to recombinant DNA molecules of *Brassica* Event MON94100. The invention also relates to transgenic *Brassica* plants, parts, seeds, cells, and agricultural products containing the *Brassica* Event MON94100 as well as methods of using the same and detecting *Brassica* Event MON94100. Transgenic *Brassica* plants, parts, seeds, and cells containing *Brassica* Event MON94100 exhibit tolerance to dicamba.

BACKGROUND OF THE INVENTION

*Brassica* crops are important in many areas of the world, and the use of herbicides for weed control in crop production is a well-established tool. Weeds compete with crops for space, nutrients, water, and light and can contaminate harvests, thus making weed control essential in agriculture. The methods of biotechnology have been used to produce transgenic *Brassica* that have the trait of tolerance to a specific herbicide due to the expression of a heterologous gene, also known as a transgene. Transgenic herbicide tolerance enables the use of an herbicide in a crop growing environment without crop injury, thus improving weed control and supporting crop yields. Transgenic traits in *Brassica* for glyphosate tolerance and glufosinate tolerance are examples of herbicide tolerance traits that have been used broadly in commercial *Brassica* production for weed control. An herbicide tolerance trait can be used alone or combined with other traits, and combinations of herbicide tolerance traits may be desirable to provide weed control options that increase grower flexibility and choice and enable the use of multiple herbicide mode of actions for controlling challenging weeds. A combination of traits can be achieved by breeding together each individual trait.

Transgenic traits are conferred by the presence in the genome of a transgenic event, which is a unique DNA sequence at a fixed location in a chromosome. An event is created by the one-time, random insertion of a transgenic expression cassette into a single, specific location in the plant genome. Each event is unique, and the expression of the transgene in a transgenic plant, part, seed, or cell, and therefore the transgene's effectiveness, for each event may be influenced by many different factors, such as the elements used in the transgenic expression cassette, the interaction of those elements, the genomic location of the transgenic insert, and the chromosomal context of the transgenic insert. For example, it has been observed that there may be wide variation in the overall level of transgene expression or in the spatial or temporal pattern of transgene expression between similarly-produced events. For this reason, it is necessary to produce and test hundreds of individual events to ultimately identify one event useful for commercial agricultural purposes. The creation and selection of an event with the qualities required for commercial crop production is a scientific process involving years of plant testing, molecular characterization, field trials, and data analysis. First, a transgenic expression cassette must be designed, tested, and optimized for expressing a specific transgene in a specific crop. Then, thousands of unique events must be produced and analyzed through multiple generations of plants, in a variety of field conditions and genetic backgrounds, to select the unique, superior event for commercial use. Such an event, once identified as having the desired transgene expression and molecular characteristics, may be used for introgressing the trait into other *Brassica* genetic backgrounds using plant breeding methods to produce a number of different *Brassica* varieties that contain the new trait combined with other desirable qualities such as native traits, high-yielding germplasm, disease tolerance, traits for hybrid seed production, and another transgenic herbicide tolerance trait(s).

BRIEF SUMMARY OF THE INVENTION

The invention provides recombinant DNA molecules comprising a sequence selected from the group consisting of SEQ ID NO:10, SEQ ID NO:9, SEQ ID NO:8, SEQ ID NO:7, SEQ ID NO:6, SEQ ID NO:5, SEQ ID NO:4, SEQ ID NO:3, SEQ ID NO:2, and SEQ ID NO: 1. In one embodiment, the recombinant DNA molecule is derived from a plant, seed, or cell comprising *Brassica* Event MON94100, a representative sample of seed comprising the event having been deposited as ATCC Accession No. PTA-125182. In another embodiment, the recombinant DNA molecule is in a plant, cell, seed, or plant part comprising *Brassica* Event MON94100, a representative sample of seed comprising the event having been deposited as ATCC PTA-125182. In another embodiment, the recombinant DNA molecule is an amplicon diagnostic for the presence of *Brassica* Event MON94100.

The invention provides a DNA molecule having a sufficient length of contiguous nucleotides of SEQ ID NO:10 to function as a DNA probe specific for SEQ ID NO:10 in a sample of DNA derived from a *Brassica* plant, *Brassica* seed, or *Brassica* cell. In one embodiment, the DNA probe comprises SEQ ID NO:13.

The invention provides a pair of DNA molecules comprising a first DNA molecule and a second DNA molecule, wherein the first and second DNA molecules each comprise a fragment of SEQ ID NO:10 and function as DNA primers when used together in an amplification reaction with DNA containing *Brassica* Event MON94100 to produce an amplicon diagnostic for *Brassica* Event MON94100 in a sample. In one embodiment, the DNA primers comprise SEQ ID NO:11 and SEQ ID NO:12.

The invention provides a method of detecting the presence of *Brassica* Event MON94100 in a sample of DNA derived from a *Brassica* plant, *Brassica* seed, or *Brassica* cell, the method comprising: contacting the sample with a DNA probe; subjecting the sample and the DNA probe to stringent hybridization conditions; and detecting hybridization of the DNA probe to a DNA molecule in the sample, wherein the hybridization of the DNA probe to the DNA molecule indicates the presence of *Brassica* Event MON94100 in the sample of DNA.

The invention provides a method of detecting the presence of *Brassica* Event MON94100 in a sample of DNA derived from a *Brassica* plant, *Brassica* seed, or *Brassica* cell, the method comprising: contacting the sample with a pair of DNA molecules that function as DNA primers; performing an amplification reaction sufficient to produce a DNA amplicon comprising a sequence selected from the group consisting of SEQ ID NO:10, SEQ ID NO:9, SEQ ID NO:8, SEQ ID NO:7, SEQ ID NO:6, SEQ ID NO:5, SEQ ID NO:4, SEQ ID NO:3, SEQ ID NO:2, and SEQ ID NO:1; and detecting the presence of the DNA amplicon, wherein the presence of the DNA amplicon indicates the presence of *Brassica* Event MON94100 in the sample.

The invention provides a method of detecting the presence of *Brassica* Event MON94100 in a sample derived from a *Brassica* plant, *Brassica* seed, or *Brassica* cell, the method comprising: contacting the sample with at least one antibody specific for the protein encoded by *Brassica* Event MON94100; and detecting binding of the antibody to the protein in the sample, wherein the binding of the antibody to the protein indicates the presence of *Brassica* Event MON94100 in the sample.

The invention provides a kit for detecting the presence of *Brassica* Event MON94100 comprising a DNA probe specific for SEQ ID NO:10, a pair of DNA primers that produce an amplicon diagnostic for *Brassica* Event MON94100, or an antibody specific for the protein encoded by *Brassica* Event MON94100.

The invention provides a plant, seed, cell, plant part, or commodity product comprising a DNA molecule comprising a sequence selected from the group consisting of SEQ ID NO:1, SEQ ID NO:2, SEQ ID NO:3, SEQ ID NO:4, SEQ ID NO:5, SEQ ID NO:6, SEQ ID NO:7, SEQ ID NO:8, SEQ ID NO:9, and SEQ ID NO:10. In one embodiment, the plant, seed, cell, or plant part is tolerant to dicamba.

The invention provides a method for controlling weeds in an area, the method comprising planting *Brassica* comprising *Brassica* Event MON94100 and applying an effective amount of dicamba to control the weeds in the area without injuring the *Brassica*. In one embodiment, the effective amount of dicamba is about 0.1 lb ae/acre to about 16 lb ae/acre over a growing season. In one embodiment, the effective amount of dicamba is about 0.5 lb ae/acre to about 2 lb ae/acre over a growing season.

The invention provides a method for controlling volunteer *Brassica* comprising *Brassica* Event MON94100 in an area, the method comprising applying an herbicidally effective amount of at least one herbicide that is not dicamba, where the herbicide application prevents growth of *Brassica* comprising *Brassica* Event MON94100. In one embodiment, the herbicide is selected from the group consisting of 2,4-D (2,4-dichlorophenoxyacetic acid), bromoxynil (3,5-dibromo-4-hydroxybenzonitrile), and MCPA amine (4-chloro-2-methylphenoxy acetic acid).

The invention provides a method of producing a plant that is tolerant to dicamba, the method comprising: breeding a plant comprising *Brassica* Event MON94100 with itself or a second plant to produce seed; and identifying progeny seed that comprise *Brassica* Event MON94100. In one embodiment, identifying progeny seed that comprise *Brassica* Event MON94100 is by growing the progeny seed to produce progeny plants; treating the progeny plants with an effective amount of dicamba; and selecting a progeny plant that is tolerant to dicamba. In one embodiment, identifying progeny seed that comprise *Brassica* Event MON94100 is by detecting the presence of *Brassica* Event MON94100 in a sample derived from the progeny seed. In one embodiment, identifying progeny seed that comprise *Brassica* Event MON94100 is by detecting the presence of at least one protein encoded by *Brassica* Event MON94100 in a sample derived from the progeny seed.

The invention provides a method of determining zygosity of a plant for *Brassica* Event MON94100 comprising: contacting a sample comprising DNA derived from the plant with a primer set capable of producing a first amplicon diagnostic for the presence of *Brassica* Event MON94100 and a second amplicon diagnostic for the wild-type *Brassica* genomic DNA not comprising *Brassica* Event MON94100; performing a nucleic acid amplification reaction; detecting the first amplicon and/or the second amplicon, wherein the presence of both amplicons indicates the sample is heterozygous for *Brassica* Event MON94100 and the presence of only the first amplicon indicates the sample is homozygous for *Brassica* Event MON94100. In one embodiment, the primer set comprises SEQ ID NO:11 and SEQ ID NO:12.

The invention provides a method of improving tolerance to dicamba in a *Brassica* plant comprising: obtaining a DNA construct comprising an expression cassette that comprises in operable linkage (a) a promoter from Peanut chlorotic streak virus, (b) a leader from Tobacco etch virus, (c) a ribulose 1,5-bisphosphate carboxylase chloroplast transit peptide from *Pisum sativum*, (d) a dicamba monooxygenase coding sequence from *Stenotrophomonas maltophilia*, and (e) a 3' UTR from *Medicago truncatula*; and inserting the DNA construct into the genome of a *Brassica* cell; regenerating the *Brassica* cell into a *Brassica* plant; and selecting a *Brassica* plant comprising the DNA construct. In one embodiment, selecting is by treating the *Brassica* plant with an effective amount of dicamba. The invention provides a *Brassica* plant, *Brassica* seed, or *Brassica* cell tolerant to dicamba obtainable by the method, wherein the *Brassica* plant, *Brassica* seed, or *Brassica* cell comprises the DNA construct. In another embodiment, the *Brassica* plant, *Brassica* seed, or *Brassica* cell produced by the method comprises SEQ ID NO:10.

BRIEF DESCRIPTION OF THE DRAWINGS

FIG. 2 represents the expression cassette of *Brassica* Event MON94100 relative to SEQ ID NO:9 with the genetic elements labeled as described in Table 1.

BRIEF DESCRIPTION OF THE SEQUENCES

Figure 1:
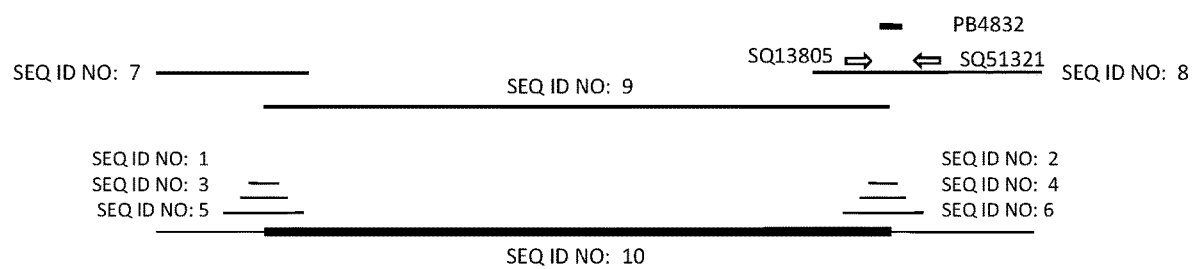
FIG. 1 represents the sequence of *Brassica* Event MON94100. Horizontal lines correspond to the positions of SEQ ID NO:1, SEQ ID NO:2, SEQ ID NO:3, SEQ ID NO:4, SEQ ID NO:5, SEQ ID NO:6, SEQ ID NO:7, SEQ ID NO:8, and SEQ ID NO:9 relative to SEQ ID NO:10; the horizontal arrows labeled SQ51321 (SEQ ID NO:11) and SQ13805 (SEQ ID NO:12) represent the approximate position of a pair of primers that can be used to detect *Brassica* Event MON94100; and the horizontal line labeled PB4832 (SEQ ID NO:13) represents the approximate position of a DNA probe that can be used to detect *Brassica* Event MON94100.

SEQ ID NO:1 is a thirty nucleotide DNA sequence representing the 5' junction of *Brassica* genomic DNA and the transgene insert. SEQ ID NO:1 corresponds to nucleotide positions 986 to 1015 of SEQ ID NO:10.

SEQ ID NO:2 is a thirty nucleotide DNA sequence representing the 3' junction of *Brassica* genomic DNA and the transgene insert. SEQ ID NO:2 corresponds to nucleotide positions 3899 to 3928 of SEQ ID NO:10.

SEQ ID NO:3 is a sixty nucleotide DNA sequence representing the 5' junction of *Brassica* genomic DNA and the transgene insert. SEQ ID NO:3 corresponds to nucleotide positions 971 to 1030 of SEQ ID NO:10.

SEQ ID NO:4 is a sixty nucleotide DNA sequence representing the 3' junction of *Brassica* genomic DNA and the transgene insert. SEQ ID NO:4 corresponds to nucleotide positions 3884 to 3943 of SEQ ID NO:10.

SEQ ID NO:5 is a one-hundred nucleotide DNA sequence representing the 5' junction of *Brassica* genomic DNA and the transgene insert. SEQ ID NO:5 corresponds to nucleotide positions 951 to 1050 of SEQ ID NO:10.

SEQ ID NO:6 is a one-hundred nucleotide DNA sequence representing the 3' junction of *Brassica* genomic DNA and the transgene insert. SEQ ID NO:6 corresponds to nucleotide positions 3864 to 3963 of SEQ ID NO:10.

SEQ ID NO:7 is a 1104 nucleotide DNA sequence representing 1000 nucleotides of the 5' flanking *Brassica* genomic DNA and 104 nucleotides of the 5' end of the transgene insert.

SEQ ID NO:8 is a 1281 nucleotide DNA sequence representing 281 nucleotides of the 3' end of the transgene insert and 1000 nucleotides of the 3' flanking *Brassica* genomic DNA.

SEQ ID NO:9 is a 2913 nucleotide DNA sequence corresponding to the transgene insert of the *Brassica* Event MON94100.

SEQ ID NO:10 is a 4913 nucleotide DNA sequence corresponding to the *Brassica* Event MON94100; the sequence contains the 5' flanking genomic DNA sequence from positions 1 to 1000, the transgenic DNA insert from positions 1001 to 3913, and the 3' flanking genomic DNA sequence from positions 3914 to 4913.

SEQ ID NO:11 is a 23 nucleotide DNA sequence corresponding to a primer referred to as SQ51321 and used to identify *Brassica* Event MON94100 DNA in a sample; it corresponds to positions 3953 to 3931 of SEQ ID NO:10.

SEQ ID NO:12 is a 26 nucleotide DNA sequence corresponding to a primer referred to as SQ13805 and used to identify *Brassica* Event MON94100 DNA in a sample; it corresponds to positions 3839 to 3864 of SEQ ID NO:10.

SEQ ID NO:13 is a 16 nucleotide DNA sequence corresponding to a probe referred to as PB4832 and used to identify *Brassica* Event MON94100 DNA in a sample; it corresponds to positions 3869 to 3881 of SEQ ID NO:10.

DETAILED DESCRIPTION OF THE INVENTION

The following definitions and methods are provided to better define the invention and to guide those of ordinary skill in the art in the practice of the invention. Unless otherwise noted, terms are to be understood according to conventional usage by those of ordinary skill in the relevant art.

Plant transformation techniques are used to insert foreign DNA (also known as transgenic DNA) randomly into a chromosome of the genome of a cell to produce a genetically engineered cell, also referred to as "transgenic" or "recombinant" cell. Using this technique, many individual cells are transformed, each resulting in a unique transgenic event due to the random insertion of the foreign DNA into the genome. A transgenic plant is then regenerated from each individual transgenic cell. This results in every cell of the transgenic plant containing the uniquely inserted transgenic event as a stable part of its genome. This transgenic plant can then be used to produce progeny plants, each containing the unique transgenic event. *Brassica* Event MON94100 was created and selected by: (i) transformation of thousands of *Brassica* cells with a DNA construct that includes the transgenic expression cassette (having been selected after the design and testing of many different expression cassettes), (ii) regeneration of a population of transgenic plants each containing a unique transgenic event, and (iii) rigorous multi-year event selection involving the testing and analysis of molecular characteristics, herbicide tolerance efficacy, and agronomic properties in a variety of genetic backgrounds for thousands of events through tens of thousands of plants. *Brassica* Event MON94100 was thus produced and selected as a uniquely superior event useful for broad-scale agronomic commercial purposes.

The act of inserting the transgenic DNA into the genome of the *Brassica* plant is accomplished by plant transformation methods known in the art and creates a new transgenic genomic DNA sequence, known as a "transgenic event" or an "event". The DNA sequence of the event consists of the inserted foreign DNA (referred to as the "transgenic insert") and the genomic DNA immediately adjacent to, or "flanking", the transgenic insert on either side of the insertion location (referred to as the "flanking DNA"). The DNA sequence of an event is unique to and specific for the event and can be readily identified when compared to other DNA sequences, such as that of other events or untransformed *Brassica* genomic DNA. *Brassica* Event MON94100 has the new and unique DNA sequence provide as SEQ ID NO:10, which contains the transgenic insert sequence provided as SEQ ID NO:9 and the 5' and 3' flanking DNA sequence provided in SEQ ID NO:7 and SEQ ID NO:8, respectively. *Brassica* Event MON94100 is thus a DNA molecule that is an integral part of the chromosome of transgenic *Brassica* cells and plants comprising the event and as such is static and may be passed on to progeny cells and plants.

The present invention also provides progeny of the original transformed cell and plant that comprise *Brassica* Event MON94100. Such progeny may be produced by cell tissue culture, by selfing of a *Brassica* plant comprising the *Brassica* Event MON94100, or by sexual outcrossing between a *Brassica* plant comprising *Brassica* Event MON94100 and another plant that does or does not contain the event. Such other plant may be a transgenic plant comprising the same or different event(s) or a nontransgenic plant, such as one from a different variety. *Brassica* Event MON94100 is passed from the original parent through each generation to the progeny.

As used herein, the term "*Brassica*" means a plant that is a member of the *Brassica* genus and includes all plant varieties that can be bred with *Brassica*. *Brassica* useful in practicing the methods of the invention include but are not limited to varieties of *Brassica napus* (commonly known as rapeseed and specific cultivars may be referred to as canola), *Brassica juncea, Brassica napobrassica, Brassica oleracea, Brassica carinata, Brassica napus, Brassica rapa*, and *Brassica campestris*, as well as any other plants belonging to the genus *Brassica* that permit breeding between *Brassica* species. Because *Brassica napus* is an allotetraploid arising from the cross and retention of both genomes of *Brassica rapa* (previously *Brassica campestris*) and *Brassica oleracea*, a *Brassica napus* plant comprising *Brassica* Event MON94100 may be used with breeding methods to introduce the *Brassica* Event MON94100, and thus the dicamba tolerance trait, into other members of the *Brassica* genus. As used herein, the term "canola" or "canola plant" refers to a

*Brassica* plant capable of being used to produce canola oil (i.e. oil meeting a specific quality designation of containing less than 2% erucic acid).

The invention provides *Brassica* Event MON94100, which provides to *Brassica* cells, plants, and seeds that comprise the event tolerance to dicamba. *Brassica* Event MON94100 contain an expression cassette for expressing the DMO protein. As used herein, an "expression cassette" or "cassette" is a recombinant DNA molecule comprising a combination of distinct elements that are to be expressed by a transformed cell. Table 1 provides a list of the elements contained in SEQ ID NO:9 and as illustrated in FIG. 2.

transformation methods. A transgene may be heterologous to the organism. The term "transgenic insert" as used herein refers to the foreign DNA inserted by plant transformation techniques into the *Brassica* genome to produce *Brassica* Event MON94100. The sequence for the transgenic insert of *Brassica* Event MON94100 is provided as SEQ ID NO:9. The term "transgenic" refers to comprising a transgene, for example a "transgenic plant" refers to a plant comprising a transgene.

As used herein, the term "heterologous" refers to a first molecule not normally associated with a second molecule or an organism in nature. For example, a DNA molecule may

TABLE 1

Description of *Brassica* Event MON94100

| Element | Position in SEQ ID NO: 10 | Description |
|---|---|---|
| 5' Flanking DNA | 1-1000 | DNA sequence flanking the 5' end of the transgenic insert |
| Right Border Region | 1001-1070 | DNA region from *Agrobacterium tumefaciens* containing the right border sequence used for transfer of the T-DNA |
| Intervening Sequence | 1071-1104 | Sequence used in DNA cloning |
| P-PCSV | 1105-1537 | Promoter for the full-length transcript of Peanut chlorotic streak virus (PSCV) that directs transcription in plant cells |
| Intervening Sequence | 1538-1557 | Sequence used in DNA cloning |
| L-TEV | 1558-1689 | 5' UTR leader sequence from the RNA of Tobacco etch virus (TEV) that is involved in regulating gene expression |
| Intervening Sequence | 1690 | Sequence used in DNA cloning |
| TS-Ps.RbcS | 1691-1933 | Ribulose 1,5-bisphosphate carboxylase (RuBisCO) chloroplast transit peptide from *Pisum sativum* |
| Intervening Sequence | 1934-1942 | Sequence used in DNA cloning |
| CS-STEma.DMO | 1943-2965 | Codon optimized sequence encoding a variant of dicamba monooxygenase (DM0) from *Stenotrophomonas maltophilia* that confers dicamba tolerance |
| Intervening Sequence | 2966-3034 | Sequence used in DNA cloning |
| T-Mt.AC | 3035-3534 | 3' UTR sequence from *Medicago truncatula* |
| Intervening Sequence | 3535-3632 | Sequence used in DNA cloning |
| Left Border Region | 3633-3913 | DNA region from *Agrobacterium tumefaciens* containing the left border sequence used for transfer of the T-DNA |
| 3' Flanking DNA | 3914-4913 | DNA sequence flanking the 3' end of the transgenic insert |

As used herein, the term "recombinant" refers to a non-natural DNA, protein, or organism that would not normally be found in nature and was created by human intervention. As used herein, a "recombinant DNA molecule" is a DNA molecule comprising a combination of DNA molecules that would not naturally occur together and is the result of human intervention, for example, a DNA molecule that is comprised of a combination of at least two DNA molecules heterologous to each other, such as a DNA molecule that comprises a transgene and the plant genomic DNA adjacent to the transgene. An example of a recombinant DNA molecule is a DNA molecule comprising at least one sequence selected from SEQ ID NO:1-10. As used herein, a "recombinant plant" is a plant that would not normally exist in nature, is the result of human intervention, and contains a transgenic DNA molecule. As a result of such genomic alteration, the recombinant plant is something new and distinctly different from the related wild-type plant. An example of a recombinant plant is a *Brassica* plant containing the *Brassica* Event MON94100.

As used herein, the term "transgene" refers to a DNA molecule artificially incorporated into an organism's genome as a result of human intervention, such as by plant be from a first species and inserted into the genome of a second species. The DNA molecule would thus be heterologous to the genome and the organism.

As used herein, the term "chimeric" refers to a single DNA molecule produced by fusing a first DNA molecule to a second DNA molecule, where neither first nor second DNA molecule would normally be found in that configuration fused to the other. The chimeric DNA molecule is thus a new DNA molecule not normally found in nature. An example of a chimeric DNA molecule is a DNA molecule comprising at least one sequence selected from SEQ ID NO:1-10.

As used herein, the term "DMO" or "dicamba monooxygenase" refers to a protein that catalyzes the deactivation of dicamba via an O-demethylation reaction to the nonherbicidal compound 3,5-dichlorosalicylic acid. Dicamba monooxygenase was originally isolated from *Stenotrophomonas maltophilia*, a microbe that is commonly found in soil rhizosphere. Exemplary sequences for nucleic acid molecules encoding dicamba monooxygenases, and the protein sequences encoded by these nucleic acid molecules, are known in the art and are described, for example, in U.S. Pat. No. 7,884,262.

As used herein, the term "isolated" refers to separating a molecule from other molecules that are normally associated with it in its native or natural state. The term "isolated" thus may refer to a DNA molecule that has been separated from other DNA molecule(s) that it is associated with it in its native or natural state. Such a DNA molecule may be present in a recombined state, such as a recombinant DNA molecule. Thus, a DNA molecule removed from its natural state and fused to another DNA molecule with which it is not normally associated would be an isolated DNA molecule. Such an isolated DNA molecule could result from the use of biotechnology techniques, such as making recombinant DNA or integrating a foreign DNA molecule into the chromosome of a cell, plant, or seed.

The invention provides DNA molecules and their corresponding DNA sequences. As used herein, the terms "DNA" and "DNA molecule" refer to a deoxyribonucleic acid (DNA) molecule. A DNA molecule may be of genomic or synthetic origin, and is by convention from the 5' (upstream) end to the 3' (downstream) end. As used herein, the term "DNA sequence" refers to the nucleotide sequence of a DNA molecule. The nomenclature used is that required by Title 37 of the United States Code of Federal Regulations § 1.822 and set forth in the tables in WIPO Standard ST.25 (1998), Appendix 2, Tables 1 and 3. By convention, the DNA sequences of the invention and fragments thereof are disclosed with reference to only one strand of the two complementary DNA sequence strands. By implication and intent, the complementary sequences of the sequences provided here (the sequences of the complementary strand), also referred to in the art as the reverse complementary sequences, are within the scope of the invention and are expressly intended to be within the scope of the subject matter claimed. Thus, as used herein references to SEQ ID NO:1-10 and fragments thereof include and refer to the sequence of the complementary strand and fragments thereof.

As used herein, the term "fragment" refers to a smaller piece of a whole. For example, fragments of SEQ ID NO:10 would include sequences that are at least about 10 consecutive nucleotides, at least about 11 consecutive nucleotides, at least about 12 consecutive nucleotides, at least about 13 consecutive nucleotides, at least about 14 consecutive nucleotides, at least about 15 consecutive nucleotides, at least about 16 consecutive nucleotides, at least about 17 consecutive nucleotides, at least about 18 consecutive nucleotides, at least about 19 consecutive nucleotides, at least about 20 consecutive nucleotides, at least about 25 consecutive nucleotides, at least about 30 consecutive nucleotides, at least about 35 consecutive nucleotides, at least about 40 consecutive nucleotides, at least about 45 consecutive nucleotides, at least about 50 consecutive nucleotides, at least about 60 consecutive nucleotides, at least about 70 consecutive nucleotides, at least about 80 consecutive nucleotides, at least about 90 consecutive nucleotides, or at least about 100 consecutive nucleotides of the complete sequence of SEQ ID NO:10.

The DNA sequence for the transgenic insert of *Brassica* Event MON94100 is provided as SEQ ID NO:9. The DNA sequence of the transgenic insert and the *Brassica* genomic DNA flanking each side of the transgenic insert is provided as SEQ ID NO:10. The DNA sequences of a portion of flanking DNA and the 5' end of the transgenic insert are provided as SEQ ID NO:1, SEQ ID NO:3, SEQ ID NO:5, and SEQ ID NO:7. The DNA sequences of a portion of flanking DNA and the 3' end of the transgenic insert are provided as SEQ ID NO:2, SEQ ID NO:4, SEQ ID NO:6, and SEQ ID NO:8.

The DNA sequence of the region spanning the connection by phosphodiester bond linkage of one end of the transgenic insert to the flanking *Brassica* genomic DNA is referred to herein as a "junction". A junction is the connection point of the transgenic insert and flanking DNA as one contiguous molecule. One junction is found at the 5' end of the transgenic insert and the other is found at the 3' end of the transgenic insert, referred to herein as the 5' and 3' junction, respectively. A "junction sequence" refers to a DNA sequence of any length that spans the 5' or 3' junction of an event. Junction sequences of *Brassica* Event MON94100 are apparent to one of skill in the art using SEQ ID NO:10. Examples of junction sequences of *Brassica* Event MON94100 are provided as SEQ ID NO:1-8. FIG. 1 illustrates the physical arrangement of SEQ ID NO:1-10 arranged from 5' to 3'. The junction sequences of *Brassica* Event MON94100 may be present as part of the genome of a plant, seed, or cell containing *Brassica* Event MON94100. The identification of any one or more of SEQ ID NO:1-8 or 10 in a sample from a plant, plant part, seed, or cell indicates that the DNA was obtained from *Brassica* containing *Brassica* Event MON94100 and is diagnostic for the presence of *Brassica* Event MON94100.

The plants, seeds, cells, plant parts, and commodity products of the invention may be used for detection of DNA or protein molecules indicative of the presence of *Brassica* Event MON94100. Provided are exemplary DNA molecules that can be used either as primers or probes for detecting the presence of *Brassica* Event MON94100 in a sample. Such primers or probes are specific for a target nucleic acid sequence and as such are useful for the identification of *Brassica* Event MON94100 by the methods described here. Detection of the presence of *Brassica* Event MON94100 may be done by using methods known in the art, such as thermal amplification of nucleic acid or nucleic acid hybridization techniques (such as northern blotting and southern analysis).

A "primer" is a DNA molecule that is designed for use in annealing or hybridization methods that involve an amplification reaction. An amplification reaction is an in vitro reaction that amplifies template DNA to produce an amplicon. As used herein, an "amplicon" is a DNA molecule that has been synthesized using amplification techniques. Amplicons of the invention have a DNA sequence comprising one or more of SEQ ID NO:1-10, or fragments thereof. A pair of primers may be used with template DNA, such as a sample of *Brassica* genomic DNA, in an amplification reaction, such as polymerase chain reaction (PCR), to produce an amplicon, where the amplicon produced would have a DNA sequence corresponding to sequence of the template DNA located between the two sites where the primers hybridized to the template. A primer is typically designed to hybridize to a complementary target DNA strand to form a hybrid between the primer and the target DNA strand. The presence of a primer is a point of recognition by a polymerase to begin extension of the primer using as a template the target DNA strand. Primer pairs refer to use of two primers binding opposite strands of a double stranded nucleotide segment for amplifying the nucleotide segment between them. Examples of primer sequences are provided as SEQ ID NO:11 (SQ51321) and SEQ ID NO:12 (SQ13805). The primer pair provided as SEQ ID NO:11 and SEQ ID NO:12 are useful as a first DNA molecule and a second DNA molecule, where the first DNA molecule is a fragment of the transgenic insert DNA sequence of SEQ ID NO:10 and the second DNA molecule is a fragment of the flanking DNA sequence of SEQ ID NO:10, and each are of sufficient length to function as DNA primers when used together in an amplification reaction with DNA containing *Brassica* Event MON94100 to produce an amplicon diagnostic for *Brassica* Event MON94100 in a sample. Primer pairs of the present invention may in certain embodiments also be defined as comprising a first and second DNA molecule, wherein the first DNA molecule is a fragment of the *Brassica* genomic portion of SEQ ID NO:10 and the second DNA molecule is a fragment of the transgene portion of SEQ ID NO:10, and each are of sufficient length to function as DNA primers when used together in an amplification reaction with DNA containing *Brassica* Event MON94100 to produce an amplicon diagnostic for *Brassica* Event MON94100 in a sample.

A "probe" is a nucleic acid molecule that is complementary to a strand of a target nucleic acid and useful in hybridization detection methods. Probes according to the invention include not only deoxyribonucleic or ribonucleic acids but also polyamides and other probe materials that bind specifically to a target DNA sequence and the detection of such binding can be useful in detecting the presence or absence of the target DNA sequence. A probe may be attached to a conventional detectable label or reporter molecule, such as a radioactive isotope, ligand, chemiluminescent agent, or enzyme. An exemplary DNA sequence useful as a probe for detecting *Brassica* Event MON94100 is provided as SEQ ID NO:13 (PB4832).

Methods for designing and using primers and probes are well known in the art. DNA molecules comprising fragments of SEQ ID NO:1-10 are useful as primers and probes for detecting *Brassica* Event MON94100 and can readily be designed by one of skill in the art using the sequences provided herein.

Probes and primers according to the invention may have complete sequence identity with the target sequence, although primers and probes differing from the target sequence that retain the ability to hybridize preferentially to target sequences may be designed by conventional methods. In order for a nucleic acid molecule to serve as a primer or probe it need only be sufficiently complementary in sequence to be able to form a stable double-stranded structure under the particular solvent and salt concentrations employed. Any conventional nucleic acid hybridization or amplification method can be used to identify the presence of transgenic DNA from *Brassica* Event MON94100 in a sample. Probes and primers are generally at least about 11 nucleotides, at least about 18 nucleotides, at least about 24 nucleotides, or at least about 30 nucleotides or more in length. Such probes and primers hybridize specifically to a target DNA sequence under stringent hybridization conditions. Stringent hybridization conditions are known in the art and described in, for example, MR Green and J Sambrook, *Molecular cloning: a laboratory manual*, 4$^{th}$ Edition, Cold Spring Harbor Laboratory Press, Cold Spring Harbor, N.Y. (2012). As used herein, two nucleic acid molecules are capable of specifically hybridizing to one another if the two molecules are capable of forming an anti-parallel, double-stranded nucleic acid structure. A nucleic acid molecule is the "complement" of another nucleic acid molecule if they exhibit complete complementarity. As used herein, two molecules exhibit "complete complementarity" if when aligned every nucleotide of the first molecule is complementary to every nucleotide of the second molecule. Two molecules are "minimally complementary" if they can hybridize to one another with sufficient stability to permit them to remain annealed to one another under at least conventional "low-stringency" conditions. Similarly, the molecules are "complementary" if they can hybridize to one another with sufficient stability to permit them to remain annealed to one another under conventional "high-stringency" conditions. Departures from complete complementarity are therefore permissible, as long as such departures do not completely preclude the capacity of the molecules to form a double-stranded structure.

Appropriate stringency conditions that promote DNA hybridization, for example, 6.0×sodium chloride/sodium citrate (SSC) at about 45° C., followed by a wash of 2.0×SSC at 50° C., are known to those skilled in the art or can be found in *Current Protocols in Molecular Biology*, John Wiley & Sons, N.Y. (1989), 6.3.1-6.3.6. For example, the salt concentration in the wash step can be selected from a low stringency of about 2.0×SSC at 50° C. to a high stringency of about 0.2×SSC at 50° C. In addition, the temperature in the wash step can be increased from low stringency conditions at room temperature, about 22° C., to high stringency conditions at about 65° C. Both temperature and salt may be varied, or either the temperature or the salt concentration may be held constant while the other variable is changed.

Provided are proteins that can be used to produce antibodies for detecting the presence of *Brassica* Event MON94100 in a sample. Such antibodies are specific for one or more of the proteins that are encoded by *Brassica* Event MON94100. The DNA sequence encoding such proteins is provided in SEQ ID NO:10 and the start positions and stop positions of the coding sequence are indicated in Table 1. The DNA sequence encoding each protein and the protein encoded by the sequence are useful to produce antibodies for detecting the presence of *Brassica* Event MON94100 by the methods described here. Detection of the presence of *Brassica* Event MON94100 may be done by using any protein detection techniques known in the art, such as western blotting, immuno-precipitation, enzyme-linked immunosorbent assay (ELISA), antibody attachment to a detectable label or reporter molecule (such as a radioactive isotope, ligand, chemiluminescent agent, or enzyme), or enzymatic action on a reporter molecule. One method provides for contacting a sample with an antibody that binds to the DMO protein encoded by *Brassica* Event MON94100 and then detecting the presence or absence of antibody binding. The binding of such antibody is diagnostic for the presence of one or more proteins encoded by *Brassica* Event MON94100.

Protein and nucleic acid detection kits for detecting the presence of *Brassica* Event MON94100 are provided. Variations on such kits can also be developed using the compositions and methods disclosed herein and the methods well known in the art of protein and nucleic acid detection. Protein and nucleic acid detection kits can be applied to methods for breeding with plants containing *Brassica* Event MON94100. Such kits contain primers or probes comprising fragments of SEQ ID NO:1-10 or antibodies specific for a protein encoded by *Brassica* Event MON94100 and may contain other elements such as one or more reaction reagents (such as nucleotides, polymerase, buffer solution). Kits may also include positive controls, negative controls, and protocols for use.

One example of a detection kit comprises at least one DNA molecule of sufficient length of contiguous nucleotides of SEQ ID NO:10 to function as a DNA probe useful for detecting the presence or absence of *Brassica* Event MON94100 in a sample. An exemplary DNA molecule sufficient for use as a probe is one comprising the sequence provided as SEQ ID NO:13. Other probes may be readily designed by one of skill in the art. Another example of a detection kit comprises at least one primer pair useful for producing an amplicon useful for detecting the presence or absence of *Brassica* Event MON94100 in a sample. Such a method may also include sequencing the amplicon or a fragment thereof. Exemplary DNA molecules sufficient for use as a primer pair are ones comprising the sequences provided as SEQ ID NO:11 and SEQ ID NO:12, respectively. Other primer pairs may be readily designed by one of skill in the art. Kits of the invention may optionally also comprise reagents for performing the detection or diagnostic reactions described herein. Another example of a detection kit comprises at least one antibody specific for at least one protein encoded by *Brassica* Event MON94100. For example, such a kit may utilize a lateral flow strip comprising reagents activated when the tip of the strip is contacted with an aqueous solution. Exemplary proteins sufficient for use in antibody production are ones encoded by the sequence provided as SEQ ID NO:10, or any fragment thereof.

The invention provides *Brassica* plants, progeny, seeds, cells, and plant parts containing *Brassica* Event MON94100, and commodity products produced using these. The plants, progeny, seeds, cells, plant parts, and commodity products of the invention contain a detectable amount of DNA having at least one of the sequences provided as SEQ ID NO:1-8 and SEQ ID NO:10.

Plants, progeny, seeds, cells, and plant parts of the invention may also contain one or more additional desirable trait(s). Such desirable traits may be transgenic traits, native traits, or traits produced by other methods such as genome editing or other conventional mutagenesis methods. Desirable traits may be combined with *Brassica* Event MON94100, by, for example, crossing a *Brassica* plant containing *Brassica* Event MON94100 with another *Brassica* plant containing the additional trait(s). Such traits include but are not limited to increased insect resistance, improved pod or seed shatter, improved oil quality, increased water use efficiency, increased yield performance, increased drought resistance, increased seed quality, improved nutritional quality, hybrid seed production, and increased herbicide tolerance, in which the trait is measured with respect to a *Brassica* plant lacking such transgenic trait.

Plants of the invention may be used to produce progeny that contain *Brassica* Event MON94100. As used herein, "progeny" includes any plant, seed, and cell comprising *Brassica* Event MON94100 inherited from an ancestor plant, indicated by the plant comprising a DNA molecule having at least one sequence selected from SEQ ID NO:1-8 and SEQ ID NO:10. Plants, seeds, and cells may be homozygous or heterozygous for *Brassica* Event MON94100. Progeny plants may be grown from seeds produced by a *Brassica* plant containing *Brassica* Event MON94100 or from seeds produced by a *Brassica* plant fertilized with pollen containing *Brassica* Event MON94100.

As used herein, a "plant part" of the invention is any part from a plant containing *Brassica* Event MON94100. Plant parts include but are not limited to tissue samples, pollen, ovule, pod, seed, flower, roots, stems, fibers, and leaves in whole or part. Plant parts may be viable or nonviable.

The invention provides a commodity product that is produced from plants containing *Brassica* Event MON94100. Commodity products of the invention contain a detectable amount of DNA comprising a DNA sequence selected from the group consisting of SEQ ID NO:1-10. As used herein, a "commodity product" refers to any composition or product which is comprised of material from plant, seed, cell, or plant part comprising *Brassica* Event MON94100. Commodity products include but are not limited to processed seeds, grains, plant parts, meal, and oil. Commodity products may be non-living plant material, that is a material that is not living and derived from a plant, seed, cell, or plant part comprising *Brassica* Event MON94100. A commodity product of the invention will contain a detectable amount of DNA corresponding to *Brassica* Event MON94100. Detection of one or more of this DNA in a sample may be used for determining the content or the source of the commodity product. Any standard method of detection for DNA molecules may be used, including methods of detection disclosed herein.

As used herein, dicamba means the herbicidal active ingredient having the chemical name 3,6-dichloro-2-methoxybenzoic acid and any salt or esters of dicamba, including, but not limited to, dicamba-Na salt, dicamba-butotyl, dicamba-diglycolamine salt, dicamba-dimethylamine salt, dicamba-dimethylammonium salt, dicamba-diethanolammonium, N,N-Bis-(aminopropyl) methylamine salt, dicamba-isopropylammonium, dicamba-potassium, dicamba-sodium, and dicamba-trolamine Dicamba may be used in a formulation comprising one or more additional herbicide(s).

As used herein, "herbicide tolerant" or "herbicide tolerance" or "tolerance" means the ability to be wholly or partially unaffected by the presence or application of one of more herbicide(s), for example to resist the toxic effects of an herbicide when applied. A cell, seed, or plant is "herbicide tolerant" or has "improved tolerance" if it can maintain at least some normal growth or phenotype in the presence of one or more herbicide(s). A trait is an herbicide tolerance trait if its presence can confer improved tolerance to an herbicide upon a cell, plant, or seed as compared to the wild-type or control cell, plant, or seed. Crops comprising an herbicide tolerance trait can continue to grow and are minimally affected by the presence of the herbicide. A protein confers "herbicide tolerance" if expression of the protein can confer improved tolerance to an herbicide upon a cell, plant, or seed as compared to the wild-type or control cell, plant, or seed. An example of an herbicide tolerance protein is dicamba monooxygenase. Herbicide tolerance may be complete or partial insensitivity to a particular herbicide and may be expressed as a percent (%) tolerance or insensitivity to a particular herbicide.

As used herein, "herbicide injury" or "injury" refers to injury to a plant because of the application of an herbicide. The "injury rate" or "percent injury" refers to a visual evaluation of injury caused by an herbicide. For *Brassica* plants containing *Brassica* Event MON94100, the plant will have decreased injury after dicamba application. Dicamba is a synthetic auxin that can affect plant growth similar to natural auxins, such as indole-3-acetic acid, but that is not metabolically regulated by the plant. As a result, dicamba treated plant tissues will continue to grow, even when the growth has a negative effect on the plant. Leaf epinasty is a noticeable downward bending or curling of leaves as a result of disturbances in their growth and is one effect of dicamba that is useful for visual evaluation of herbicide injury.

As used herein, a "weed" is any undesired plant. A plant may be considered generally undesirable for agriculture or horticulture purposes (for example, *Amaranthus* species) or may be considered undesirable in a particular situation (for example, a crop plant of one species in a field of a different species, also known as a volunteer plant). Weeds are commonly known in the art and vary by geography, season, growing environment, and time. Lists of weed species are available from agricultural and scientific societies (such as the Weed Science Society of America and the Canadian Weed Science Society), government agencies (such as the United States Department of Agriculture), and industry and farmer associations (such as the Canola Council of Canada).

The invention provides methods for controlling weeds in an area for *Brassica* cultivation by applying dicamba, where seeds or plants comprising *Brassica* Event MON94100 are planted in the area before, at the time of, or after applying the herbicide and the herbicide application prevents or inhibits weed growth and does not injure the *Brassica* plants. The plant growth area may or may not comprise weed seeds or plants at the time of herbicide application. The dicamba used in the methods of the invention can be applied alone or in combination with one or more herbicide(s) during the growing season. The herbicide(s) used in the methods of the invention can be applied in combination with one or more herbicide(s) temporally (for example, as a tank mixture or in sequential applications), spatially (for example, at different times during the growing season including before and after *Brassica* seed planting), or both. For example, a method for controlling weeds is provided that consists of planting seed comprising *Brassica* Event MON94100 in an area and applying an herbicidally effective amount over the growing season of dicamba, alone or in any combination with another herbicide, for the purpose of controlling weeds in the area without injuring the plants containing *Brassica* Event MON94100. Such application may be pre-planting (any time prior to planting seed containing *Brassica* Event MON94100, including for burn-down purposes, that is application to emerging or existing weeds prior to seed plant), pre-emergence (any time after seed containing *Brassica* Event MON94100 is planted and before plants containing *Brassica* Event MON94100 emerge), or post-emergence (any time after plants containing *Brassica* Event MON94100 emerge). Multiple applications of dicamba, or a combination of dicamba and one or more other herbicide(s) together or individually, may be used over a growing season, for example, two applications (such as a pre-planting application and a post-emergence application, or a pre-emergence application and a post-emergence application) or three or more applications (such as a pre-planting application and two post-emergence applications).

Herbicide application in practicing the methods of the invention may be at the recommended commercial rate or any fraction or multiple thereof, such as twice the recommended commercial rate. Herbicide rates may be expressed as acid equivalent per pound per acre (lb ae/acre) or active ingredient per pound per acre (lb ai/acre), depending on the herbicide and the formulation. An herbicidally effective amount of dicamba for use in the area for controlling weeds should consist of a range from about 0.1 lb ae/ac to as much as about 16 lb ae/ac over a growing season (for example, dicamba could be applied at a rate of about 0.5 lb ae/acre to about 2.0 lb ae/acre).

The invention provides methods for controlling volunteer *Brassica* comprising *Brassica* Event MON94100 in an area for crop cultivation by applying an herbicidally effective amount of another herbicide, such as a synthetic auxin selected from the group consisting of 2,4-D (2,4-dichlorophenoxyacetic acid), bromoxynil (3,5-dibromo-4-hydroxybenzonitrile), and MCPA amine (4-chloro-2-methylphenoxy acetic acid), where the herbicide application prevents growth of *Brassica* comprising *Brassica* Event MON94100. An herbicidally effective amount of 2,4-D herbicide for use in the area for controlling volunteer *Brassica* could be applied at a rate of about 0.1 lb ae/ac to as much as about 16 lb ae/ac over a growing season (for example, 2,4-D could be applied at a rate of about 0.5 lb ae/acre to about 2.0 lb ae/acre) over a growing season. An herbicidally effective amount of bromoxynil herbicide for use in the area for controlling volunteer *Brassica* could be applied at a rate of about 0.1 lb ae/ac to as much as about 16 lb ae/ac over a growing season (for example, bromoxynil could be applied at a rate of about 0.5 lb ae/acre to about 2.0 lb ae/acre) over a growing season. An herbicidally effective amount of MCPA amine herbicide for use in the area for controlling volunteer *Brassica* could be applied at a rate of about 0.1 lb ae/ac to as much as about 16 lb ae/ac over a growing season (for example, MCPA amine could be applied at a rate of about 0.5 lb ae/acre to about 2.0 lb ae/acre) over a growing season.

Methods for producing plants and seeds containing *Brassica* Event MON94100 are provided. Plants may be bred using any method known in the art, for example, descriptions of breeding methods that are commonly used can be found in W R Fehr, in *Breeding Methods for Cultivar Development*, Wilcox J. ed., American Society of Agronomy, Madison Wis. (1987). Plants may be self-pollinated (also known as "selfing") or cross-pollinated (also known as "crossing"). Plants containing *Brassica* Event MON94100 may be self-pollinated to generate a true breeding line of plants that are homozygous for *Brassica* Event MON94100. Selfing results in progeny known as "inbred" and can be used to produce inbred lines that are genetically uniform. Alternatively, plants containing *Brassica* Event MON94100 may be cross-pollinated (bred with another plant that is transgenic or nontransgenic) to produce a varietal or a hybrid seed. Seed and progeny plants made by the methods of the invention contain *Brassica* Event MON94100. Application of one or more herbicide for which *Brassica* Event MON94100 confers tolerance may be used to select progeny that contain *Brassica* Event MON94100. Alternatively, progeny may be analyzed using diagnostic methods to select for plants or seeds containing *Brassica* Event MON94100. Progeny may be varietal or hybrid plants; may be grown from seeds produced by a plant containing *Brassica* Event MON94100 or from seeds produced by a plant fertilized with pollen from a plant containing *Brassica* Event MON94100; and may be homozygous or heterozygous for *Brassica* Event MON94100.

Plants, progeny, seeds, cells, and plant parts of the invention may also contain one or more additional *Brassica* trait(s) or transgenic event(s). Such additional trait(s) or transgenic event(s) include, but are not limited to, increased insect resistance, increased water use efficiency, increased yield performance, increased drought resistance, increased seed quality, improved nutritional quality, hybrid seed production, male sterility, and herbicide tolerance, in which the trait is measured with respect to a *Brassica* plant lacking such transgenic trait. *Brassica* transgenic events are known to one of skill in the art; for example, a list of such traits is provided by the United States Department of Agriculture's (USDA) Animal and Plant Health Inspection Service (APHIS). Two or more transgenic events may be combined in a progeny seed or plant by crossing two parent plants each comprising one or more transgenic event(s), collecting progeny seed, and selecting for progeny seed or plants that contain the two or more transgenic events; these steps may then be repeated until the desired combination of transgenic events in a progeny is achieved. Back-crossing to a parental plant and out-crossing with a non-transgenic plant are also contemplated, as is vegetative propagation.

A deposit of a representative sample of at least 2,500 seeds comprising *Brassica* Event MON94100 has been made according to the Budapest Treaty with the American Type Culture Collection (ATCC®) Patent Depository having an address at 10801 University Boulevard, Manassas, Va. 20110 (USA). The ATCC Patent Deposit Designation (accession number) for seeds comprising Brassica Event MON94100 is PTA-125182 and the date of deposit was Aug. 21, 2018. The deposit has been accepted under the Budapest Treaty and will be maintained in the depository for a period of 30 years, or 5 years after the last request, or for the effective life of the patent, whichever is longer.

As used herein, the term "comprising" means "including but not limited to".

EXAMPLES

The following examples are included to more fully describe the invention. Summarized are the construction and testing of six different expression constructs, the production of 2,775 unique transformation events, and the analysis of millions of individual plants over five years through the rigorous molecular, agronomic, and field testing required for the creation and ultimate selection of *Brassica* Event MON94100.

It should be appreciated by those of skill in the art that many modifications can be made in the specific examples which are disclosed and still obtain a similar result. Certain agents which are both chemically and physiologically related may be substituted for the agents described herein while achieving the same or similar results. All such substitutions and modifications apparent to those skilled in the art are deemed to be within the scope of the invention.

Example 1: Expression Construct Design, Event Production, and R0 and R1 Plant Testing This example describes the design of six different expression constructs for dicamba tolerance, the production of thousands of unique *Brassica* events using plant vectors containing these constructs, and the analysis and testing of the resulting transgenic *Brassica* plants over two generations (R0 and R1).

Six expression constructs were designed and cloned into plant transformation vectors. Four single expression cassette constructs (DT-1, DT-2, DT-3, and DT-4) were designed with each having a unique combination of expression elements and DMO transgenes operably linked, allowing for testing three different promoters, three different CTPs, and two different DMO variants in *Brassica* plants. Two double expression cassette constructs (DT-5 and DT-6) were designed with each having a unique combination of expression elements and DMO transgenes operably linked, allowing for testing two different promoters, two different CTPs, and two different DMO variants transgene in combination with the same CP4-EPSPS expression cassette. Constructs are shown in Table 2. The six expression constructs were then cloned into plant transformation vectors.

TABLE 2

Configurations for Expression Constructs

| | | cassette 1 (DMO) | | | cassette 2 (CP4) | |
| --- | --- | --- | --- | --- | --- | --- |
| Construct | Promoter | Gene of Interest | 3' UTR | Promoter | Gene of Interest | 3' UTR |
| DT-1 | PCSV | Ps.RbcS/DMOc | Mt.AC | | | |
| DT-2 | P-1 | CTP-1/DMOc | Mt.AC | | | |
| DT-3 | P-2 | CTP-2/DMOw | Mt.AC | | | |
| DT-4 | P-2 + E | CTP-2/DMOw | Mt.AC | | | |
| DT-5 | P-2 + E | CTP-2/DMOw | Mt.AC | P-3 | CTP-3/CP4 | UTR-1 |
| DT-6 | PCSV | Ps.RbcS/DMOc | Mt.AC | P-3 | CTP-3/CP4 | UTR-1 |

The six plant transformation vectors were used for *Agrobacterium*-mediated transformation of *Brassica napus* variety 65037 Restorer line (Canada Plant Breeders' Rights Application 06-5517) using methods known in the art to produce 2,775 unique transformation events. Each transformation event was made by the random insertion of a transgene insert into the *Brassica* genome at a unique location. R0 plants were then regenerated from the transgenic cells, and rooted plants with normal phenotypic characteristics were transferred to soil for growth and further assessment.

The 2,775 R0 plants were analyzed for having a single, intact copy of the transgenic insert and absence of vector backbone sequence. From this initial molecular analysis, 201 unique events were identified as the highest quality events for advancement.

Selections of plants representing the DT-1, DT-2, and DT-3 constructs were used for R0 trait efficacy (dicamba tolerance) testing in the greenhouse. Dicamba was applied at spray rates of either 1.0 lb ae/acre of Clarity® herbicide (2× rate) or 2.0 lb ae/acre of Clarity herbicide (4× rate) at the V3 growth stage. Dicamba-induced plant injury was evaluated visually, based on estimation of plant epinasty (bending or twisting of the leaf), growth reduction, chlorosis, and necrosis. Plants that showed greater than 20% injury were discarded. R0 plants for the DT-1 and DT-3 constructs showed tolerance (less than 20% injury) to the 2× rate in greenhouse sprays, but R0 plants for the DT-2 construct all showed dicamba injury greater than 20% to the 2× rate. Analysis of this data resulted in the decision to not advance any events produced using the DT-2 construct.

Combining the molecular analysis data and the R0 dicamba tolerance testing, from the initial 2,775 unique transformation events produced using the six transformation vectors, 206 unique events were selected for advancement. The R0 plants for the selected events were self-pollinated to produce homozygous seed for R1 testing.

Greenhouse testing for dicamba tolerance was conducted with R1 plants for the 169 unique events. Dicamba was applied at spray rates of 1120 g ae/ha of Clarity herbicide (2× rate) at the V3 growth stage. For double-cassette events (those produced using DT-5 or DT-6), dicamba was applied as a tank-mix of glyphosate at spray rates of 3600 g ae/ha of Roundup® (2× rate). Dicamba-induced plant injury was evaluated as described above. Plants were prioritized for advancement based on low dicamba symptomology.

R1 plants showed average injury rate of 7.48% for the DT-1 construct; 72.66% for the DT-3 construct; 20.7% for the DT-5 construct; and 33.4% for the DT-6 construct. However, individual events with less than 20% injury were advanced unless the injury was epinasty. This resulted in the selection of 9 events from the DT-1 construct, 17 events from the DT-5 construct, and 9 events from the DT-6 construct in addition to one event from the DT-4 construct.

Thirty-six (36) unique events were selected for advancement to F1 field trials based on the analysis of data from an initial molecular analysis (for copy number, intact insert, and the absence of vector backbone) and R0 and R1 greenhouse evaluation for herbicide tolerance. Data for this is summarized in Table 3. The R1 plants for the selected events were cross-pollinated with conventional plants to produce seed.

TABLE 3

Number of Unique Events Advanced in R0 and R1 Plants

| Construct | Unique Events Produced | Events advanced from molecular analysis and R0 efficacy tests | Events advanced from R1 efficacy tests |
|---|---|---|---|
| DT-1 | 558 | 17 | 9 |
| DT-2 | 459 | 0 | 0 |
| DT-3 | 537 | 28 | 0 |
| DT-4 | 18 | 1 | 1 |
| DT-5 | 579 | 51 | 17 |
| DT-6 | 624 | 109 | 9 |
| Total | 2,775 | 184 | 36 |

Example 2: First-Season Field Trials

This example describes the first-season field trials of plants containing each of the 36 unique events advanced from the R1 analysis. For each unique event, in the first-season field trials thousands of plants were tested in the field over the course of two years in 8 to 13 different locations for trait efficacy (dicamba tolerance), agronomic performance, and yield. These data were analyzed to compare the performance of each event in field conditions across all plants and all locations. The data from the first-season field trials were then used to select superior events for advancement to second-season field trials.

Hybrid F1 plants for field trials were produced by cross-pollinating a female parental *Brassica napus* line with the R1 or R2 plants for the selected events to produce hybrid F1 seed (hemizygous for the event). For each of the two years during which first-season field trials were conducted, a different female parental *Brassica napus* line was cross-pollinated by the R1 plants for the selected events to produce F1 hybrid seed. The female parental line was also cross-pollinated with a non-transgenic plant from the same genetic background as the R1 line for use as a control. This strategy ensured testing of the events in a variety of female parental lines and use of an appropriate control for comparisons.

In the first-season testing, 36 unique events were selected for field trials from the original 2,775 events. These 36 events represented the best events from four different expression constructs: nine events for construct DT-1, one event for construct DT-4, seventeen events for construct DT-5, and nine events for construct DT-6. The first-season trials were conducted over two years, but for each event the first-season agronomic performance field trials were done concurrently (during the same season) with the first-season trait efficacy field trials. All field trials used a randomized complete block design and were conducted at 8 to 13 different locations in North America.

In first-season trait efficacy trials, F1 hybrid plants were assessed for tolerance to dicamba. Two dicamba applications were tested for events for all: Treatment 1 (TRT1) comprised a pre-emergent treatment of 2.4 kg ae/ha (2× commercial rate) of BANVEL® II and a post-emergent treatment at the 3 leaf growth stage (V3) of 1.2 kg ae/ha (2× commercial rate) of BANVEL® II; Treatment 2 (TRT2) comprised a pre-emergent treatment of 2.4 kg ae/ha (2× commercial rate) of BANVEL® II post-emergent treatment at V3 of 1.2 kg ae/ha (2× commercial rate) of BANVEL® II, and a post-emergent treatment at first flower of 1.2 kg ae/ha (2× commercial rate) of BANVEL® II. At seven days following each application (V3 or first flower, respectively), the percentage herbicide-induced plant injury was evaluated visually, based on estimation of plant epinasty (bending or twisting of the leaf), growth reduction, chlorosis, and necrosis. Agronomic scoring was collected throughout the field trial season. At the end of the season, yield as pounds/acre (lb/ac) was determined.

The trait efficacy data from the first-season field trials was compiled. For each unique event, meta-analysis of the aggregate data across all locations and all individual plants for first-season trait efficacy field trials was analyzed for comparison of the hybrid injury ratings. Table 4 provides the average injury rating for each event for the two dicamba treatment regimens across all locations (NA indicates data for treatment not available). Meta-analysis of the trait efficacy field trials over each season showed that on average plants from all events had low dicamba injury, but events from the DT-1 and DT-4 constructs performed exceptionally well with lower injury ratings.

TABLE 4

Meta-Analysis of Injury Rating from First-Season Trait Efficacy Field Trials

| Construct | Event | TRT1 % Injury | TRT1 Std. Error | TRT2 % Injury | TRT2 Std. Error | Reps | Locations | Total Seeds |
|---|---|---|---|---|---|---|---|---|
| DT-1 | MON94100 | <1% | NA | <1% | NA | 3 | 11 | ~49,500 |
| DT-1 | 170060 | <1% | NA | <1% | NA | 3 | 11 | ~49,500 |
| DT-1 | 169242 | <1% | NA | <1% | NA | 3 | 11 | ~49,500 |
| DT-1 | 169934 | <1% | NA | <1% | NA | 3 | 11 | ~49,500 |
| DT-1 | 170631 | <1% | NA | <1% | NA | 3 | 11 | ~49,500 |
| DT-1 | 169703 | <1% | NA | <1% | NA | 3 | 11 | ~49,500 |
| DT-1 | 169250 | <1% | NA | <1% | NA | 3 | 11 | ~49,500 |
| DT-1 | 169954 | <1% | NA | <1% | NA | 3 | 11 | ~49,500 |
| DT-1 | 170020 | <1% | NA | <1% | NA | 3 | 11 | ~49,500 |

TABLE 4-continued

Meta-Analysis of Injury Rating from First-Season Trait Efficacy Field Trials

| Construct | Event | TRT1 % Injury | TRT1 Std. Error | TRT2 % Injury | TRT2 Std. Error | Reps | Locations | Total Seeds |
|---|---|---|---|---|---|---|---|---|
| DT-4 | 68403 | <1% | NA | <1% | NA | 3 | 11 | ~49,500 |
| DT-5 | 26258 | NA | NA | 3.59 | 1.63 | 3 | 8 | ~36,000 |
| DT-5 | 40784 | NA | NA | 2.92 | 1.56 | 3 | 8 | ~36,000 |
| DT-5 | 40804 | NA | NA | 2.36 | 1.56 | 3 | 8 | ~36,000 |
| DT-5 | 40807 | NA | NA | 2.81 | 1.59 | 3 | 8 | ~36,000 |
| DT-5 | 40810 | NA | NA | 2.31 | 1.56 | 3 | 8 | ~36,000 |
| DT-5 | 40819 | NA | NA | 1.88 | 1.56 | 3 | 8 | ~36,000 |
| DT-5 | 40834 | NA | NA | 3.33 | 1.56 | 3 | 8 | ~36,000 |
| DT-5 | 40847 | NA | NA | 3.96 | 1.56 | 3 | 8 | ~36,000 |
| DT-5 | 43118 | NA | NA | 2.69 | 1.56 | 3 | 8 | ~36,000 |
| DT-5 | 43166 | NA | NA | 2.92 | 1.56 | 3 | 8 | ~36,000 |
| DT-5 | 43167 | NA | NA | 3.14 | 1.56 | 3 | 8 | ~36,000 |
| DT-5 | 43185 | NA | NA | 2.94 | 1.57 | 3 | 8 | ~36,000 |
| DT-5 | 43206 | NA | NA | 2.41 | 1.61 | 3 | 8 | ~36,000 |
| DT-5 | 43237 | NA | NA | 2.28 | 1.56 | 3 | 8 | ~36,000 |
| DT-5 | 43296 | NA | NA | 2.08 | 1.56 | 3 | 8 | ~36,000 |
| DT-5 | 43299 | NA | NA | 3.75 | 1.56 | 3 | 8 | ~36,000 |
| DT-5 | 43325 | NA | NA | 2.08 | 1.56 | 3 | 8 | ~36,000 |
| DT-6 | 61734 | NA | NA | 1.88 | 1.56 | 3 | 8 | ~36,000 |
| DT-6 | 61737 | NA | NA | 2.29 | 1.56 | 3 | 8 | ~36,000 |
| DT-6 | 61757 | NA | NA | 2.71 | 1.56 | 3 | 8 | ~36,000 |
| DT-6 | 75997 | NA | NA | 1.97 | 1.58 | 3 | 8 | ~36,000 |
| DT-6 | 76023 | NA | NA | 2.58 | 1.60 | 3 | 8 | ~36,000 |
| DT-6 | 83521 | NA | NA | 2.29 | 1.56 | 3 | 8 | ~36,000 |
| DT-6 | 83528 | NA | NA | 2.00 | 1.61 | 3 | 8 | ~36,000 |
| DT-6 | 83535 | NA | NA | 2.50 | 1.56 | 3 | 8 | ~36,000 |
| DT-6 | 83613 | NA | NA | 2.08 | 1.57 | 3 | 8 | ~36,000 |

The yield data from the first-season trait efficacy field trials was compiled. For each unique event, meta-analysis of the aggregate yield data across all locations and all individual plants for first-season trait efficacy field trials was analyzed for comparison. Table 5 provides the average yield pounds/acre (lbs/ac) for each event for the two dicamba treatment regimens across all locations (NA indicates data for treatment not available). Meta-analysis of the yield for the trait efficacy field trials over each season showed that on average plants from all events had yield comparable to unsprayed control plants. Meta-analysis of the compiled data for plants comprising events from the DT-6 construct had noticeably lower yield on average than plants comprising events from the DT-5 construct.

TABLE 5

Meta-Analysis of Yield from First-Season Trait Efficacy Field Trials

| Construct | Event | No Spray | TRT1 | TRT2 | Std. Error | Reps | Locations | Total Seeds |
|---|---|---|---|---|---|---|---|---|
| DT-1 | MON94100 | 2842.4 | 2938.1 | 2872.9 | 125.0 | 3 | 11 | ~49,500 |
| DT-1 | 170060 | 2921.3 | 2871.0 | 2839.4 | 125.0 | 3 | 11 | ~49,500 |
| DT-1 | 169242 | 2807.9 | 2855.8 | 2909.9 | 125.0 | 3 | 11 | ~49,500 |
| DT-1 | 169934 | 2869.2 | 2842.6 | 2874.5 | 125.0 | 3 | 11 | ~49,500 |
| DT-1 | 170631 | 2838.1 | 2819.6 | 2857.5 | 125.0 | 3 | 11 | ~49,500 |
| DT-1 | 169703 | 2808.9 | 2833.8 | 2879.0 | 125.0 | 3 | 11 | ~49,500 |
| DT-1 | 169250 | 2759.2 | 2790.4 | 2845.0 | 125.0 | 3 | 11 | ~49,500 |
| DT-1 | 169954 | 2743.3 | 2660.7 | 2690.8 | 125.0 | 3 | 11 | ~49,500 |
| DT-1 | 170020 | 2754.3 | 2743.9 | 2737.3 | 125.0 | 3 | 11 | ~49,500 |
| DT-4 | 68403 | 2480.4 | 2331.9 | 2524.7 | 125.0 | 3 | 11 | ~49,500 |
| DT-5 | 26258 | 2441.5 | NA | 2543.7 | 201.8 | 3 | 8 | ~36,000 |
| DT-5 | 40784 | 2504.0 | NA | 2492.7 | 199.6 | 3 | 8 | ~36,000 |
| DT-5 | 40804 | 2496.7 | NA | 2554.6 | 200.2 | 3 | 8 | ~36,000 |
| DT-5 | 40807 | 2458.0 | NA | 2539.3 | 200.9 | 3 | 8 | ~36,000 |
| DT-5 | 40810 | 2503.8 | NA | 2557.0 | 199.9 | 3 | 8 | ~36,000 |
| DT-5 | 40819 | 2442.6 | NA | 2617.8 | 199.6 | 3 | 8 | ~36,000 |
| DT-5 | 40834 | 2529.3 | NA | 2623.6 | 199.9 | 3 | 8 | ~36,000 |
| DT-5 | 40847 | 2496.0 | NA | 2513.6 | 199.6 | 3 | 8 | ~36,000 |
| DT-5 | 43118 | 2451.0 | NA | 2567.3 | 199.6 | 3 | 8 | ~36,000 |
| DT-5 | 43166 | 2411.2 | NA | 2517.0 | 199.6 | 3 | 8 | ~36,000 |
| DT-5 | 43167 | 2515.6 | NA | 2550.5 | 199.6 | 3 | 8 | ~36,000 |
| DT-5 | 43185 | 2478.5 | NA | 2528.4 | 200.2 | 3 | 8 | ~36,000 |
| DT-5 | 43206 | 2426.8 | NA | 2570.1 | 201.8 | 3 | 8 | ~36,000 |
| DT-5 | 43237 | 2317.5 | NA | 2503.8 | 199.6 | 3 | 8 | ~36,000 |
| DT-5 | 43296 | 2536.0 | NA | 2544.6 | 199.6 | 3 | 8 | ~36,000 |
| DT-5 | 43299 | 2396.9 | NA | 2601.3 | 199.6 | 3 | 8 | ~36,000 |
| DT-5 | 43325 | 2618.5 | NA | 2554.6 | 199.6 | 3 | 8 | ~36,000 |
| DT-6 | 61734 | 2381.7 | NA | 2577.1 | 199.6 | 3 | 8 | ~36,000 |

TABLE 5-continued

Meta-Analysis of Yield from First-Season Trait Efficacy Field Trials

| Construct | Event | No Spray | TRT1 | TRT2 | Std. Error | Reps | Locations | Total Seeds |
|---|---|---|---|---|---|---|---|---|
| DT-6 | 61737 | 2484.6 | NA | 2557.8 | 199.6 | 3 | 8 | ~36,000 |
| DT-6 | 61757 | 2471.8 | NA | 2477.4 | 199.6 | 3 | 8 | ~36,000 |
| DT-6 | 75997 | 2527.7 | NA | 2482.6 | 200.6 | 3 | 8 | ~36,000 |
| DT-6 | 76023 | 2501.8 | NA | 2528.9 | 201.8 | 3 | 8 | ~36,000 |
| DT-6 | 83521 | 2486.7 | NA | 2526.5 | 199.6 | 3 | 8 | ~36,000 |
| DT-6 | 83528 | 2589.1 | NA | 2515.5 | 201.3 | 3 | 8 | ~36,000 |
| DT-6 | 83535 | 2415.4 | NA | 2627.3 | 199.6 | 3 | 8 | ~36,000 |
| DT-6 | 83613 | 2486.6 | NA | 2549.2 | 200.2 | 3 | 8 | ~36,000 |

In first-season agronomic performance trials, F1 hybrid plants were assessed for agronomic performance and yield. The plots were maintained weed free and the test herbicide (dicamba or dicamba and glyphosate) was not applied during the growing season. Agronomic scoring was collected for all events: Early Vigor, Emergence Uniformity, Date of First Flower, Date of End of Flower, Plant Height, Maturity Date, Actual Grain Weight Harvested, Percent Grain Moisture, Harvest Date, and, if applicable, Standability, Pod Shattering, *Sclerotinia* Incidence, and Disease and Insect Pressure. Agronomic scoring was collected throughout the field trial season. At the end of the season, agronomic yield as pounds/acre (lb/ac) was determined.

The yield data from the first-season agronomic performance field trials was compiled. For each unique event, meta-analysis of the aggregate yield data across all locations and all individual plants for first-season agronomic field trials was analyzed for comparison. Table 6 provides the average yield as pounds/acre (lbs/ac) for each event across all locations. Meta-analysis of the yield for the agronomic field trials over each season showed that on average plants from all events had yield comparable to unsprayed control plants, with the exception of the 68403 event from the DT-4 construct and the 43166 and 43237 events from the DT-5 construct which had noticeably lower yield. Four events from the DT-1 construct had noticeably lower agronomic yield than the other five events from the DT-1 construct.

TABLE 6

Meta-Analysis of Yield from First-Season Agronomic Field Trials

| Construct | Event | Control Yield | Std. Error | Event Yield | Std. Error | Reps | Locations | Total Seeds |
|---|---|---|---|---|---|---|---|---|
| DT-1 | MON94100 | 3112.63 | 238.21 | 3044.03 | 235.80 | 4 | 13 | ~78,000 |
| DT-1 | 170060 | 3112.63 | 238.30 | 3040.19 | 235.80 | 4 | 13 | ~78,000 |
| DT-1 | 169242 | 3112.63 | 238.30 | 3096.13 | 235.80 | 4 | 13 | ~78,000 |
| DT-1 | 169934 | 3112.63 | 238.12 | 3024.22 | 235.80 | 4 | 13 | ~78,000 |
| DT-1 | 170631 | 3112.63 | 238.21 | 3023.24 | 235.80 | 4 | 13 | ~78,000 |
| DT-1 | 169703 | 3112.63 | 238.30 | 2975.86 | 235.80 | 4 | 13 | ~78,000 |
| DT-1 | 169250 | 3112.63 | 238.39 | 2957.04 | 235.80 | 4 | 13 | ~78,000 |
| DT-1 | 169954 | 3112.63 | 238.12 | 2942.50 | 235.80 | 4 | 13 | ~78,000 |
| DT-1 | 170020 | 3112.63 | 238.30 | 2920.91 | 235.80 | 4 | 13 | ~78,000 |
| DT-4 | 68403 | 3112.63 | 238.12 | 2835.35 | 235.80 | 4 | 13 | ~78,000 |
| DT-5 | 26258 | 2625.86 | 156.04 | 2542.26 | 161.48 | 4 | 9 | ~54,000 |
| DT-5 | 40784 | 2625.86 | 156.04 | 2519.60 | 161.75 | 4 | 9 | ~54,000 |
| DT-5 | 40804 | 2625.86 | 156.04 | 2452.60 | 161.48 | 4 | 9 | ~54,000 |
| DT-5 | 40807 | 2625.86 | 156.04 | 2577.59 | 162.11 | 4 | 9 | ~54,000 |
| DT-5 | 40810 | 2625.86 | 156.04 | 2561.00 | 161.75 | 4 | 9 | ~54,000 |
| DT-5 | 40819 | 2625.86 | 156.04 | 2674.75 | 161.75 | 4 | 9 | ~54,000 |
| DT-5 | 40834 | 2625.86 | 156.04 | 2597.13 | 161.48 | 4 | 9 | ~54,000 |
| DT-5 | 40847 | 2625.86 | 156.04 | 2562.87 | 161.48 | 4 | 9 | ~54,000 |
| DT-5 | 43118 | 2625.86 | 156.04 | 2586.34 | 161.48 | 4 | 9 | ~54,000 |
| DT-5 | 43166 | 2625.86 | 156.04 | 2461.79 | 161.48 | 4 | 9 | ~54,000 |
| DT-5 | 43167 | 2625.86 | 156.04 | 2526.65 | 161.75 | 4 | 9 | ~54,000 |
| DT-5 | 43185 | 2625.86 | 156.04 | 2552.44 | 161.48 | 4 | 9 | ~54,000 |
| DT-5 | 43206 | 2625.86 | 156.04 | 2465.98 | 161.48 | 4 | 9 | ~54,000 |
| DT-5 | 43237 | 2625.86 | 156.04 | 2436.54 | 161.75 | 4 | 9 | ~54,000 |
| DT-5 | 43296 | 2625.86 | 156.04 | 2569.12 | 161.48 | 4 | 9 | ~54,000 |
| DT-5 | 43299 | 2625.86 | 156.04 | 2555.65 | 161.75 | 4 | 9 | ~54,000 |
| DT-5 | 43325 | 2625.86 | 156.04 | 2507.47 | 162.11 | 4 | 9 | ~54,000 |
| DT-6 | 61734 | 2625.86 | 156.04 | 2615.07 | 161.48 | 4 | 9 | ~54,000 |
| DT-6 | 61737 | 2625.86 | 156.04 | 2599.27 | 162.11 | 4 | 9 | ~54,000 |
| DT-6 | 61757 | 2625.86 | 156.04 | 2596.95 | 161.48 | 4 | 9 | ~54,000 |
| DT-6 | 75997 | 2625.86 | 156.04 | 2603.56 | 161.48 | 4 | 9 | ~54,000 |
| DT-6 | 76023 | 2625.86 | 156.04 | 2538.96 | 161.84 | 4 | 9 | ~54,000 |
| DT-6 | 83521 | 2625.86 | 156.04 | 2566.44 | 161.75 | 4 | 9 | ~54,000 |
| DT-6 | 83528 | 2625.86 | 156.04 | 2559.93 | 161.48 | 4 | 9 | ~54,000 |
| DT-6 | 83535 | 2625.86 | 156.04 | 2536.29 | 161.75 | 4 | 9 | ~54,000 |
| DT-6 | 83613 | 2625.86 | 156.04 | 2577.33 | 161.48 | 4 | 9 | ~54,000 |

The data accumulated from the field trials with hybrid plants assessing (1) trait efficacy for commercial rates of dicamba tolerance, and (2) agronomic performance was analyzed for the 36 events tested for constructs DT-1, DT-4, DT-5, and DT-6. This analysis for each event was combined with the results of the in-depth molecular characterization described in Example 3 to select events for advancement to second-season field trials.

Example 3: Molecular Characterization

This Example describes the extensive molecular characterization of selected events that was done concurrently with the field trails. The molecular characterization of each event was used to determine whether an event should be selected for advancement.

DNA and RNA analysis of events was conducted using a variety of techniques known in the art. Southern blot analysis was performed on genomic DNA to confirm that transgenic plants contained a single copy of the entire transgene insert without any vector backbone. DNA amplification and sequencing was used to confirm the composition and intactness of the insert sequence in the transgenic insert for each event. The DNA flanking each end of the transgenic insert (the 5' and 3' ends) was sequenced, and the respective junctions were determined. Northern analysis was done to detect and measure mRNA transcripts of the dmo gene and cp4 gene (if applicable) in transgenic plants for each event.

Protein analysis of plants comprising each event was conducted using techniques known in the art. N-terminal protein sequencing of the DMO protein purified from transgenic plants containing each event was done to confirm the recombinant protein sequence. Western blot analysis was conducted on protein extracts from plants containing each event to confirm the DMO protein was being produced. An enzyme-linked immunosorbent assay (ELISA) was used to determine protein levels in the leaf, seed, roots, and pollen of plants for the DMO protein.

The insertion site of each event in the genome was analyzed. The flanking sequence was used for bioinformatic analysis of the chromosomal location of the event, and the insertion site for each event was mapped to the publicly-available Brassica napus genome (Boulos Chalhoub, et al. "Early allopolyploid evolution in the post-Neolithic Brassica napus oilseed genome", Science, Vol 345 Issue 6199 (22 Aug. 2014). DNA amplification across the wild-type allele in the genome was conducted using primers specific to the flanking regions of each event. The wild-type insertion site sequence was used to map the unique site of transgene integration for the event to the Brassica napus reference genome.

Analysis of the in-depth molecular characterization for each event was combined with the trait efficacy and agronomic performance data from the first-season field trials for each event. Using this combined information, 13 unique events were selected for advancement from the 36 tested in first-season field trials. After analysis, none of the 9 events for construct DT-6 were selected for advancement; 10 of the 17 events from DT-5 were not advanced; and thirteen unique events were selected for advancement with five events for construct DT-1, one event for construct DT-4, and seven events for construct DT-5.

Example 4: Second-Season Field Trials

This example describes the second-season field trials of plants containing each of the 13 unique events advanced from the first-season field trials. For each unique event, in the second-season field trials thousands of plants were tested in the field over the course of two years in multiple locations for trait efficacy (dicamba and glyphosate tolerance), agronomic performance, and yield. These data were analyzed to compare the performance of each event in field conditions across all plants and all locations. The data from the second-season field trials were then used to select superior events for advancement to third-season field trials.

Hybrid F1 plants for the second-season field trials were produced by cross-pollinating a female parental Brassica napus line with the R2 plants for the selected events to produce hybrid F1 seed (hemizygous for the event). Parental female lines containing a commercial glyphosate tolerance event (indicated as RR) were used for crossing with R2 plants comprising the DT-1 and DT-4 constructs, thus producing F1 plants tolerant to both dicamba and glyphosate. For each of the two years during which second-season field trials were conducted, 1-3 different female parental Brassica napus lines were cross-pollinated by the R2 plants for the selected events to produce F1 hybrid seed. The female parental line was also cross-pollinated with a non-transgenic plant from the same genetic background as the R2 line for use as a control. This strategy ensured testing of the events in a variety of female parental lines and use of an appropriate control for comparisons.

In the second-season testing, the 13 unique events selected for testing represented five events for construct DT-1, one event for construct DT-4, and seven events for construct DT-5. The second-season trials were conducted over two years, but for each event the second-season agronomic performance field trials were done concurrently (during the same season) with the second-season trait efficacy field trials. All field trials used a randomized complete block design and were conducted at 4 to 9 different locations in North America.

In second-season trait efficacy trials, F1 hybrid plants were assessed for tolerance to dicamba and glyphosate. Plants were treated with a post-emergent application (as a tank-mixture) of 1.2 kg ae/ha (2× commercial rate) of dicamba (BANVEL II) and 1.8 kg ae/ha of glyphosate (Roundup) at V3 followed by of 1.2 kg ae/ha (2× commercial rate) of dicamba (BANVEL II) and 1.8 kg ae/ha of glyphosate (Roundup) at first flower. At seven days following each application (V3 or first flower, respectively), the percentage herbicide-induced plant injury was evaluated visually, based on estimation of plant epinasty (bending or twisting of the leaf), growth reduction, chlorosis, and necrosis. Agronomic scoring was collected throughout the field trial season. At the end of the season, yield as pounds/acre (lb/ac) was determined.

The trait efficacy data from the second-season field trials was compiled. For each unique event, meta-analysis of the aggregate data across all locations and all individual plants for trait efficacy field trials was analyzed for comparison of the hybrid injury ratings. Table 7 provides the average injury rating for each event for the treatment regimen across all locations. Meta-analysis of the trait efficacy field trials over each season showed that on average plants from the DT-1 and DT-4 constructs performed exceptionally well with lower herbicide injury ratings.

TABLE 7

Meta-Analysis of Injury Rating from Second-Season Trait Efficacy Field Trials

| Construct | Event(s) | % Injury | Std. Error | Reps | Locations | Total Seeds |
|---|---|---|---|---|---|---|
| DT-1 | RR × MON94100 | 6.67 | 1.65 | 3 | 4 | ~18,000 |
| DT-1 | RR × 170060 | 7.9 | 1.75 | 3 | 4 | ~18,000 |
| DT-1 | RR × 169242 | 11.05 | 1.83 | 3 | 4 | ~18,000 |
| DT-1 | RR × 169934 | 6.49 | 1.61 | 3 | 4 | ~18,000 |
| DT-1 | RR × 170631 | 7.09 | 1.80 | 3 | 4 | ~18,000 |
| DT-4 | RR × 68403 | 9.65 | 1.82 | 3 | 8 | ~36,000 |
| DT-5 | 40807 | 16.9 | 2.41 | 3 | 9 | ~81,000 |
| DT-5 | 40810 | 16.72 | 2.40 | 3 | 9 | ~81,000 |
| DT-5 | 40819 | 16.92 | 2.43 | 3 | 9 | ~81,000 |
| DT-5 | 40834 | 17.71 | 2.43 | 3 | 9 | ~81,000 |
| DT-5 | 43185 | 17.47 | 2.39 | 3 | 9 | ~81,000 |
| DT-5 | 43296 | 17.84 | 2.39 | 3 | 9 | ~81,000 |
| DT-5 | 43325 | 17.31 | 2.39 | 3 | 9 | ~81,000 |

The yield data from the second-season trait efficacy field trials was compiled. For each unique event, meta-analysis of the aggregate yield data across all locations and all individual plants for second-season trait efficacy field trials was analyzed for comparison. Table 8 provides the average yield pounds/acre (lbs/ac) for sprayed and unsprayed plants (control) for each event for the treatment regimen across all locations. Meta-analysis of the yield for the trait efficacy field trials over each season showed that on average plants containing *Brassica* Event MON94100 had the highest yield compared to plants for the other 12 events when sprayed with dicamba and glyphosate.

TABLE 8

Meta-Analysis of Yield from Second-Season Trait Efficacy Field Trials

| Construct | Event(s) | Control | Sprayed | Std. Error | Reps | Locations | Total Seeds |
|---|---|---|---|---|---|---|---|
| DT-1 | RR × MON94100 | 2785.1 | 2829.4 | 141 | 3 | 4 | ~18,000 |
| DT-1 | RR × 170060 | 2714.6 | 2350.9 | 148.4 | 3 | 4 | ~18,000 |
| DT-1 | RR × 169242 | 2846.0 | 2658.3 | 154.3 | 3 | 4 | ~18,000 |
| DT-1 | RR × 169934 | 2870.1 | 2736.4 | 137.3 | 3 | 4 | ~18,000 |
| DT-1 | RR × 170631 | 2762.2 | 2731.4 | 148.9 | 3 | 4 | ~18,000 |
| DT-4 | RR × 68403 | 2539.8 | 2464.1 | 199.9 | 3 | 8 | ~36,000 |
| DT-5 | 40807 | 2908.4 | 2457.9 | 230.5 | 3 | 6 | ~54,000 |
| DT-5 | 40810 | 2842.8 | 2443.0 | 230.2 | 3 | 6 | ~54,000 |
| DT-5 | 40819 | 2831.7 | 2328.2 | 230.3 | 3 | 6 | ~54,000 |
| DT-5 | 40834 | 2921.3 | 2447.9 | 230.3 | 3 | 6 | ~54,000 |
| DT-5 | 43185 | 2870.3 | 2429.5 | 230.1 | 3 | 6 | ~54,000 |
| DT-5 | 43296 | 2823.0 | 2425.8 | 230.1 | 3 | 6 | ~54,000 |
| DT-5 | 43325 | 2969.1 | 2533.8 | 230.1 | 3 | 6 | ~54,000 |

In second-season agronomic performance trials, F1 hybrid plants were assessed for agronomic performance and yield as described in Example 2. At the end of the season, agronomic yield as pounds/acre (lb/ac) was determined. The yield data from the second-season agronomic performance field trials was compiled. For each unique event, meta-analysis of the aggregate yield data across all locations and all individual plants for second-season agronomic field trials was analyzed for comparison. Table 9 provides the average yield as pounds/acre (lbs/ac) for each event across all locations. Meta-analysis of the yield for the agronomic field trials over each season showed that on average plants from all events had yield comparable to control plants, except for a noticeably lower yield for event 40819 for the DT-5 construct.

TABLE 9

Meta-Analysis of Yield from Second-Season Agronomic Field Trials

| Construct | Event | Control Yield | Std. Error | Event Yield | Std. Error | Reps | Locations | Total Seeds |
|---|---|---|---|---|---|---|---|---|
| DT-1 | MON94100 | 2513.27 | 171.57 | 2453.28 | 172.49 | 4 | 9 | ~162,000 |
| DT-1 | 170060 | 2513.27 | 171.57 | 2515.65 | 175.52 | 4 | 9 | ~162,000 |
| DT-1 | 169242 | 2513.27 | 171.57 | 2501.70 | 171.97 | 4 | 9 | ~162,000 |

TABLE 9-continued

Meta-Analysis of Yield from Second-Season Agronomic Field Trials

| Construct | Event | Control Yield | Std. Error | Event Yield | Std. Error | Reps | Locations | Total Seeds |
|---|---|---|---|---|---|---|---|---|
| DT-1 | 169934 | 2513.27 | 171.57 | 2484.87 | 171.30 | 4 | 9 | ~162,000 |
| DT-1 | 170631 | 2513.27 | 171.57 | 2453.91 | 173.71 | 4 | 9 | ~162,000 |
| DT-1 | 169703 | 2513.27 | 171.57 | 2411.77 | 173.89 | 4 | 9 | ~162,000 |
| DT-1 | 169250 | 2513.27 | 171.57 | 2493.73 | 175.22 | 4 | 9 | ~162,000 |
| DT-1 | 169954 | 2513.27 | 171.57 | 2455.10 | 177.10 | 4 | 9 | ~162,000 |
| DT-1 | 170020 | 2513.27 | 171.57 | 2457.30 | 187.83 | 4 | 9 | ~162,000 |
| DT-4 | 68403 | 2585.18 | 156.04 | 2589.55 | 161.48 | 4 | 6 | ~54,000 |
| DT-5 | 40807 | 2647.04 | 386.40 | 2590.38 | 375.82 | 4 | 6 | ~72,000 |
| DT-5 | 40810 | 2647.04 | 386.40 | 2629.07 | 378.73 | 4 | 6 | ~72,000 |
| DT-5 | 40819 | 2647.04 | 386.40 | 2502.89 | 375.93 | 4 | 6 | ~72,000 |
| DT-5 | 40834 | 2647.04 | 386.40 | 2585.98 | 375.73 | 4 | 6 | ~72,000 |
| DT-5 | 43185 | 2647.04 | 386.40 | 2670.88 | 378.73 | 4 | 6 | ~72,000 |
| DT-5 | 43296 | 2647.04 | 386.40 | 2606.68 | 378.73 | 4 | 6 | ~72,000 |
| DT-5 | 43325 | 2647.04 | 386.40 | 2685.73 | 378.73 | 4 | 6 | ~72,000 |

The data accumulated from the molecular analysis and from the field trials with hybrid plants assessing (1) trait efficacy for commercial rates of dicamba and glyphosate tolerance, and (2) agronomic performance, was analyzed for the 13 events tested for constructs DT-1, DT-4, and DT-5. Analysis of the trait efficacy, agronomic performance, and yield data from the second-season field trial for each event was combined with the results of the in-depth molecular characterization described in Example 3 to select four unique events for testing in third-season field trials. The four unique events represented two events for construct DT-1 and two events for construct DT-5.

Example 5: Third-Season Field Trials

This example describes the third-season field trials of plants containing each of the 4 unique events advanced from the second-season field trials. For each unique event, in the third-season field trials thousands of plants were tested in the field over the course of two years in multiple locations for trait efficacy (dicamba tolerance), agronomic performance, and yield. These data were analyzed to compare the performance of each event in field conditions across all plants and all locations. The data from the third-season field trials were then used to select a superior event for commercialization.

Hybrid F1 plants for the third-season field trials were produced by cross-pollinating a female parental *Brassica napus* line with the R2 or R3 plants for the selected events to produce hybrid F1 seed (hemizygous for the event). For each of the two years during which third-season field trials were conducted, 2-3 different female parental *Brassica napus* lines were cross-pollinated by the R1 plants for the selected events to produce F1 hybrid seed. The female parental line was also cross-pollinated with a non-transgenic plant from the same genetic background as the R2 or R3 line for use as a control. This strategy ensured testing of the events in a variety of female parental lines and use of an appropriate control for comparisons.

The third-season trials were conducted over two years, but for each event the third-season agronomic performance field trials were done concurrently (during the same season) with the third-season trait efficacy field trials. All field trials used a randomized complete block design and were conducted at 5 to 10 different locations in North America.

In third-season trait efficacy trials, F1 hybrid plants were assessed for tolerance to dicamba using the XtendiMax® herbicide and as described in Example 2, and, at the end of the season, yield as pounds/acre (lb/ac) was determined. The trait efficacy data from the third-season field trials was compiled. For each unique event, meta-analysis of the aggregate data across all locations and all individual plants for trait efficacy field trials was analyzed for comparison of the hybrid injury ratings. Table 10 provides the average injury rating for each event for the treatment regimen across all locations. Meta-analysis of the trait efficacy field trials over each season showed that on average plants from the DT-1 constructs performed exceptionally well with lower herbicide injury ratings.

TABLE 10

Meta-Analysis of Injury Rating from Third-Season Trait Efficacy Field Trials

| Construct | Event | TRT1 % Injury | TRT1 Std. Error | TRT2 % Injury | TRT2 Std. Error | Reps | Locations | Total Seeds |
|---|---|---|---|---|---|---|---|---|
| DT-5 | 43296 | NA | NA | 1.03 | 1.12 | 3 | 9 | ~121,500 |
| DT-5 | 43325 | NA | NA | 1.11 | 1.12 | 3 | 9 | ~121,500 |
| DT-1 | MON94100 | 0.13 | 0.22 | 0.23 | 0.06 | 4 | 10 | ~120,000 |
| DT-1 | 170060 | 0.02 | 0.21 | 0.25 | 0.07 | 4 | 10 | ~120,000 |

The yield data from the third-season trait efficacy field trials was compiled. For each unique event, meta-analysis of the aggregate yield data across all locations and all individual plants for third-season trait efficacy field trials was analyzed for comparison. Table 11 provides the average yield pounds/acre (lbs/ac) for each event for the two dicamba treatment regimens across all locations (NA indicates data for treatment not available). Meta-analysis of the yield for the trait efficacy field trials showed that on average plants from all events had yield comparable to unsprayed control plants.

TABLE 11

Meta-Analysis of Yield from Third-Season Trait Efficacy Field Trials

| Construct | Event | No Spray | TRT1 | TRT2 | Std. Error | Reps | Locations | Total Seeds |
|---|---|---|---|---|---|---|---|---|
| DT-5 | 43296 | 3902.7 | NA | 3742.3 | 287.6 | 3 | 5 | ~67,500 |
| DT-5 | 43325 | 3948.2 | NA | 4125.9 | 292.7 | 3 | 5 | ~67,500 |
| DT-1 | MON94100 | 3795.2 | 3849.9 | 3764.4 | 202.3 | 4 | 10 | ~120,000 |
| DT-1 | 170060 | 3771.9 | 3942.8 | 3887.5 | 204.2 | 4 | 10 | ~120,000 |

In third-season agronomic performance trials, F1 hybrid plants were assessed for agronomic performance and yield as described in Example 2, and, at the end of the season, agronomic yield as pounds/acre (lb/ac) was determined. The yield data from the third-season agronomic performance field trials was compiled. For each unique event, meta-analysis of the aggregate yield data across all locations and all individual plants for third-season agronomic field trials was analyzed for comparison. Table 12 provides the average yield as pounds/acre (lbs/ac) for each event across all locations. Meta-analysis of the yield for the agronomic field trials showed that on average plants from all events had yield comparable to unsprayed control plants, with no statistically significant difference.

TABLE 12

Meta-Analysis of Yield from Third-Season Agronomic Field Trials

| Construct | Event | Control Yield | Std. Error | Event Yield | Std. Error | Reps | Locations | Total Seeds |
|---|---|---|---|---|---|---|---|---|
| DT-5 | 43296 | 3864.59 | 490.07 | 3717.83 | 493.24 | 4 | 5 | ~90,000 |
| DT-5 | 43325 | 3999.59 | 490.12 | 3857.2 | 490.34 | 4 | 5 | ~90,000 |
| DT-1 | MON94100 | 3818.3 | 277.82 | 3787.57 | 279.88 | 6 | 10 | ~180,000 |
| DT-1 | 170060 | 3818.3 | 277.82 | 3952.31 | 280.28 | 6 | 10 | ~180,000 |

The data accumulated from the molecular analysis and from the third-season field trials was analyzed for the four events. Analysis of the trait efficacy, agronomic performance, and yield data from the third-season field trial for each event was combined with the results of the in-depth molecular characterization described in Example 3 to assess the events. In addition, the desirability of a dicamba tolerance trait that is not molecularly linked to another herbicide tolerance trait was considered. The configuration of a single dicamba tolerance expression cassette permits increased flexibility and choice for farmers in volunteer control, weed control, agronomics, and crop rotation. Two events representing the DT-1 construct were advanced for meta-analysis of the composite data from the three seasons of field trials.

Example 6: Meta-Analysis of Composite Field Trial Data

This example describes the meta-analysis of all the field trial data for the two final events. This allowed a larger comparison of the trait performance and yield impact under field conditions in hybrid plants across many years, dozens of locations, and hundreds of thousands of plants.

Meta-analysis of the trait efficacy was conducted by compiling the data for first and third seasons, across all locations for the two selected events from construct DT-1. This allowed a larger comparison of the hybrid injury ratings. Table 13 provides the average injury rating for each event for each treatment. Meta-analysis of the trait efficacy field trials showed that both events for the DT-1 construct had exceptionally low herbicide injury ratings for both treatments.

TABLE 13

Meta-Analysis of Injury Rating from Trait Efficacy Field Trials Compiled

| Event | Treatment | Injury Rating | Std. Error |
|---|---|---|---|
| MON94100 | TRT1 | 0.28 | 0.25 |
| MON94100 | TRT2 | 0.52 | 0.25 |
| 170060 | TRT1 | 0.37 | 0.2 |
| 170060 | TRT2 | 0.43 | 0.2 |

Meta-analysis of all the yield data from the trait efficacy field trials was conducted by compiling the data for first and third seasons, across all locations for the two selected events from construct DT-1. Table 14 provides the average yield change as pounds per acre (lb/ac) (calculated as the yield difference between sprayed and unsprayed plants containing the same event) as pounds/acre for each event for each treatment. Meta-analysis of the yield from the trait efficacy field trials showed that the MON94100 event performed exceptionally well resulting in higher yield on average in both treatments than the 170060 event. This data is critical in selecting an elite commercial event and demonstrated the outstanding performance of plants containing the Brassica Event MON94100 in field conditions under dicamba application.

TABLE 14

Meta-Analysis of Yield from Trait Efficacy Field Trials Compiled

| Event | Treatment | Yield Change | Std. Error |
|---|---|---|---|
| MON94100 | TRT1 | 82.75 | 59.76 |
| MON94100 | TRT2 | 23.18 | 59.56 |
| 170060 | TRT1 | 62.13 | 67.64 |
| 170060 | TRT2 | 17.98 | 67.69 |

Meta-analysis of all the yield data from the agronomic field trials was conducted by compiling the data for all three seasons, across all locations for the two selected events from construct DT-1 and the control plants. This allowed a larger comparison of the yield data in the absence of dicamba application. Table 15 provides the average yield as pounds/acre for each event for each treatment. Meta-analysis of the yield data from the agronomic field trails showed that MON94100 and 170060 provided yield comparable to the control plants in unsprayed conditions, with no statistical difference in yield for plants containing either of these events when compared to the control plants.

TABLE 15

Meta-Analysis of Yield from Agronomic Field Trials Compiled

| Event | Year | Estimated Yield | Std. Error |
|---|---|---|---|
| MON94100 | Across | 3035.34 | 168.22 |
| 170060 | Across | 3046.47 | 168.3 |
| Control | Across | 3083.59 | 167.49 |

Analysis of the cumulative data demonstrated the superiority of *Brassica* Event MON94100 compared to the 170060 event for dicamba tolerance and crop yield under herbicide application conditions and resulted in selection of this event as a superior event useful for commercial purposes.

Example 7: Detection of *Brassica* Event MON94100

This Example describes the detection of *Brassica* Event MON94100. Detection of *Brassica* Event MON94100 in a sample can be done using DNA, RNA, or protein detection techniques. Exemplary detection methods and materials are provided below. DNA sequence information for *Brassica* Event MON94100 is provided herein as SEQ ID NOs:1-10. The transgenic insert of *Brassica* Event MON94100 contains the elements described in Table 1.

Detection may be used to determine the presence or absence of *Brassica* Event MON94100 in a sample and may indicate the number of genomic copies of *Brassica* Event MON94100 (that is, hemizygous, homozygous, or heterozygous) in a sample of genomic DNA. An event specific endpoint Applied Biosystems™ TAQMAN® thermal amplification method (Thermo Fisher Scientific) was developed to identify *Brassica* Event MON94100 in a sample. The DNA primers and probe used in the endpoint assay are primers SQ51321 (SEQ ID NO:11), SQ13805 (SEQ ID NO:12), and 6-FAM™ labeled probe PB4832 (SEQ ID NO:13). 6-FAM (6-carboxyfluorescein) is a fluorescent dye product of Applied Biosystems (Foster City, Calif.) attached to the DNA probe. For TAQMAN MGB™ probes, the 5' exonuclease activity of Taq DNA polymerase cleaves the probe from the 5'-end, between the fluorophore and quencher. When hybridized to the target DNA strand, quencher and fluorophore are separated enough to produce a fluorescent signal, thus releasing fluorescence. SQ51321 and SQ13805 when used with these reaction methods and PB4832 produce a DNA amplicon that is diagnostic for *Brassica* Event MON94100. The controls for this analysis should include a positive control containing *Brassica* Event MON94100, a negative control from non-transgenic *Brassica*, and a negative control that contains no template DNA. Additionally, a control for the PCR reaction should optimally include Internal Control Primers and an Internal Control Probe, specific to a single copy gene in the *Brassica* genome. These assays are optimized for use with the Applied Biosystems GeneAmp® PCR System 9700 (Thermo Fisher Scientific) run at maximum speed, but other equipment may be used.

An example of conditions useful with TAQMAN methods for detection of *Brassica* Event MON94100 is as follows. Step 1: 18 megohm water adjusted for final volume of 5 µl. Step 2: 2.28 IA of 2× Universal Master Mix (dNTPs, enzyme, buffer) to a 1× final concentration. Step 3: 0.05 µl Event Primer-1 (SQ51321) and Event Primer-2 (SQ13805) (resuspended in 18 megohm water to a concentration of 100 uM for each primer) to 0.9 µM final concentration. Step 4: 0.01 µl Event 6-FAM MGB Probe PB4832 (resuspended in 18 megohm water to a concentration of 100 µM) to 0.2 µM final concentration. Step 5: 0.05 µl Internal Control Primer-1 and Internal Control Primer-2 Mix (resuspended in 18 megohm water to a concentration of 100 µM for each primer) to 0.9 µM final concentration. Step 6: 0.01 µl Internal Control VIC™ Probe (resuspended in 18 megohm water to a concentration of 100 µM) to 0.2 µM final concentration. Step 7: 2.5 µl Extracted DNA (template) for each sample with one each of the following comprising: (a) Leaf Samples to be analyzed; (b) Negative control (non-transgenic DNA); (c) Negative water control (no template); and (d) Positive control *Brassica* containing *Brassica* Event MON94100 DNA. Step 8: Thermocycler Conditions as follows: one cycle at 95° C. for 20 seconds; forty cycles of 95° C. for 3 seconds then 60° C. for 20 seconds; and final cycle of 10° C.

A zygosity assay is developed to determine whether a plant comprising *Brassica* Event MON94100 is heterozygous or homozygous for the event or the wild-type allele. An amplification reaction assay can be designed using the sequence information provided herein. For example, such a PCR assay would include design of at least three primers: primer-1, primer-2, and primer-3, where primer-1 is specific to *Brassica* genomic DNA on the 3' flanking DNA of *Brassica* Event MON94100; primer-2 is specific to *Brassica* Event MON94100 transgenic insert; and primer-3 is specific to the wild-type allele. When used as a primer pair in an amplification reaction, primer-1 with primer-2 will produce a PCR amplicon specific for *Brassica* Event MON94100. When used as a primer pair in an amplification reaction, primer-1 with primer-3 will produce a PCR amplicon specific for wild-type allele. In a PCR reaction performed on *Brassica* genomic DNA, the respective PCR amplicons generated from primer-1+primer-2 and that generated from primer-1+primer-3 will differ in sequence and size of the amplicon. When the three primers are included in a PCR reaction with DNA extracted from a plant homozygous for *Brassica* Event MON94100, only the primer-1+primer-2 amplicon (specific for the *Brassica* MON94100 insertion) will be generated. When the three primers are included in a PCR reaction with DNA extracted from a plant heterozygous for *Brassica* Event MON94100, both the primer-1+primer-2 amplicon (specific for the *Brassica* MON94100 insertion) and the primer-1+primer-3 amplicon (specific for wild-type allele or absence of the *Brassica* MON94100 insertion) will be generated. When the three primers are mixed together in a PCR reaction with DNA extracted from a plant that is null for *Brassica* Event MON94100 (that is wild-type), only the primer-1+primer-3 amplicon (specific for wild-type allele) will be generated. The amplicons produced using the PCR reaction may be identified or distinguished using any method known in the art.

Another zygosity assay for *Brassica* Event MON94100 is a TAQMAN thermal amplification reaction. For this type of assay, in addition to primers as described above, the assay would include two fluorescently labeled probes. Probe-1 would be specific for *Brassica* Event MON94100, and probe-2 would be specific for a *Brassica* plant that is null for *Brassica* Event MON94100 (wild-type), and where the two probes contain different fluorescent labels, for example the 6-FAM-label or VIC™-label. When used in a TAQMAN reaction, primer-1+primer-2+probe-1 will produce a first fluorescent signal specific for *Brassica* Event MON94100 and primer-1+primer-3+probe-2 will produce a second fluorescent signal specific for wild-type *Brassica*. When the three primers and two probes are included in a TAQMAN reaction with DNA extracted from a plant homozygous for *Brassica* Event MON94100, only the first fluorescent signal (specific to primer-1+primer-2+probe-1) will be generated. When the three primers are included in a TAQMAN reaction with DNA extracted from a plant heterozygous for *Brassica* Event MON94100, both the first fluorescent signal (specific to primer-1+primer-2+probe-1) and the second fluorescent signal (specific to primer-1+primer-3+probe-2) will be generated. When the three primers are mixed together in a TAQMAN reaction with DNA extracted from a plant which is null for *Brassica* Event MON94100 (wild-type), only the second fluorescent signal (specific to primer-1+primer-3+probe-2) will be generated.

Another method to detect the presence of *Brassica* Event MON94100 in a plant sample would be Southern analysis. One of skill in art would understand how to design Southern hybridization probe(s) specific for *Brassica* Event MON94100 and a second southern hybridization probe specific for a *Brassica* plant which is null for *Brassica* Event MON94100 (wild-type). With Southern analysis, a signal detected only from the first Southern hybridization probe will be indicative of a plant homozygous for *Brassica* Event MON94100; a signal detected from both the first Southern hybridization probe and the second Southern hybridization probe will be indicative of a plant heterozygous for *Brassica* Event MON94100; and a signal detected only from the second Southern hybridization probe will be indicative that the DNA was extracted from a plant that is null for *Brassica* Event MON94100 (wild-type).

Another example of a detection kit comprises at least one antibody specific for at least one protein encoded by *Brassica* Event MON94100. For example, such a kit may utilize a lateral flow strip comprising reagents activated when the tip of the strip is contacted with an aqueous solution. Exemplary proteins sufficient for use in antibody production are ones encoded by the sequence provided as SEQ ID NO:10, or any fragment thereof.

A protein detection method is developed to determine whether a sample is from a plant, seed, cell, or plant part comprising *Brassica* Event MON94100. At least one antibody specific for at least one protein encoded by *Brassica* Event MON94100 is used to detect a protein encoded by *Brassica* Event MON94100 in a sample. A detection kit comprising one or more antibodies specific for one or more proteins encoded by *Brassica* Event MON94100 may utilize a lateral flow strip containing reagents activated when the tip of the strip is contacted with an aqueous solution. Samples of *Brassica* tissue may be ground up and protein extracted for analysis using water or an aqueous buffer (for example, phosphate buffered saline containing detergent and bovine serum albumin). Following centrifugation, the aqueous supernatant is analyzed using the ELISA method in a sandwich format on a lateral flow strip containing an absorbent pad. Detection is activated by dipping the tip of the strip into the aqueous solution containing the sample to be tested. The aqueous solution is carried up the strip by capillary action and solubilizes gold labeled antibodies on the strip. The gold labeled antibodies are specific for at least one protein encoded by *Brassica* Event MON94100 and will bind to an epitope on the protein in the sample to form an antibody-antigen complex. The gold labeled antibody-antigen complex is then carried up the strip to a nitrocellulose membrane. The membrane comprises a test line of immobilized antibodies that bind to a second, separate epitope on the protein encoded by *Brassica* Event MON94100, causing a visible line to appear across the test strip if the protein encoded by *Brassica* Event MON94100 is present in the sample.

Example 8: Volunteer Control

This example describes methods for controlling plants comprising *Brassica* Event MON94100. For purposes of volunteer control, any herbicide to which plants comprising *Brassica* Event MON94100 is sensitive would be useful.

An exemplary herbicide for purposes of volunteer control would include a synthetic auxin herbicide other than dicamba. The sensitivity of plants comprising *Brassica* Event MON94100 to synthetic auxin herbicides other than dicamba provides farmers with the capability to remove unwanted dicamba-tolerant *Brassica* (this is, those comprising *Brassica* Event MON94100) from an environment. Such environment may or may not include other desirable crops or *Brassica* that do not contain *Brassica* Event MON94100.

Plants comprising *Brassica* Event MON94100 and non-transgenic plants of the same germplasm as a control were grown in a greenhouse in a randomized complete block design. Plants were sprayed at V3 stage with one of four synthetic auxin herbicides: dicamba (as XtendiMax®), 2,4-D amine (dimethylamine salt of 2,4-dichlorophenoxy-acetic acid), bromoxynil (3,5-dibromo-4-hydroxybenzonitrile as Buctril®), and MCPA amine (4-chloro-2-methylphenoxy acetic acid) in a randomized pattern. Plant injury rate was taken at 9 days after treatment.

After spraying with dicamba at the commercial rate (1×), plants comprising *Brassica* Event MON94100 had no injury and control plants had 21.3% injury. However, when sprayed with the other three synthetic auxin herbicides (2,4-D amine, bromoxynil and MCPA) at either 1× or 2× rates, both plants comprising *Brassica* Event MON94100 and control plants showed a 70% to 90% injury rate. This confirmed that plants comprising *Brassica* Event MON94100 and control plants respond similarly to the three auxin herbicides. Data are shown in Table 16.

TABLE 16

| Plant Injury Rates (%) After Herbicide Spray | | | | | |
| --- | --- | --- | --- | --- | --- |
| Treatment | Concentration | MON94100 | Std. Error for MON94100 | Control | Std. Error for Control |
| Dicamba | 600 g ae/ha (1X) | 0.0 | 0 | 21.3 | 3.6 |
| 2,4-D amine 4 | 1064 g ai/ha (1X) | 74.5 | 5.1 | 73.0 | 4.7 |
|  | 2128 g ai/ha (2X) | 83.5 | 2.4 | 82.0 | 2.5 |

TABLE 16-continued

Plant Injury Rates (%) After Herbicide Spray

| Treatment | Concentration | MON94100 | Std. Error for MON94100 | Control | Std. Error for Control |
|---|---|---|---|---|---|
| Bromoxynil | 280 g ai/ha (1X) | 80.5 | 4.8 | 83.3 | 6.1 |
|  | 560 g ai/ha (2X) | 90.3 | 7.2 | 90.6 | 6.5 |
| MCPA amine | 840 g ai/ha (1X) | 73.0 | 2.5 | 71.5 | 3.7 |
|  | 1680 g ai/ha (2X) | 86.5 | 3.3 | 85.0 | 1.6 |

A deposit of a representative sample of seed comprising Brassica Event MON94100 has been made according to the Budapest Treaty with the American Type Culture Collection (ATCC®) Patent Depository having an address at 10801 University Boulevard, Manassas, Va. 20110 (USA). The ATCC Patent Deposit Designation (accession number) for seeds comprising Brassica Event MON94100 is Accession No. PTA-125182 and the date of deposit was Aug. 21, 2018. The deposit will be maintained in the depository for a period of 30 years, or 5 years after the last request, or for the effective life of the patent, whichever is longer.

What is claimed is:

1. A recombinant DNA molecule comprising a sequence selected from the group consisting of SEQ ID NO:10, SEQ ID NO:9, SEQ ID NO:8, SEQ ID NO:7, SEQ ID NO:6, SEQ ID NO:5, SEQ ID NO:4, SEQ ID NO:3, SEQ ID NO:2, and SEQ ID NO:1.

2. The recombinant DNA molecule of claim 1, wherein the recombinant DNA molecule:

a) comprises SEQ ID NO:1 and SEQ ID NO:2; or
b) comprises SEQ ID NO:3 and SEQ ID NO:4.

3. A *Brassica napus* plant, seed, cell, plant part, or commodity product comprising a DNA molecule comprising SEQ ID NO: 1 and SEQ ID NO: 2 flanking a nucleic acid sequence encoding a dicamba mono-oxygenase (DMO) protein.

* * * * *